United States Patent
Kimura et al.

(10) Patent No.: US 12,298,319 B2
(45) Date of Patent: May 13, 2025

(54) METHOD FOR MEASURING ALPHA VALUE OF MUSCARINIC M1 RECEPTOR POSITIVE ALLOSTERIC MODULATORS

(71) Applicant: Takeda Pharmaceutical Company Limited, Osaka (JP)

(72) Inventors: Haruhide Kimura, Kanagawa (JP); Yuu Sako, Kanagawa (JP); Satoru Matsuda, Kanagawa (JP); Yuji Shimizu, Kanagawa (JP); Emi Kurimoto, Kanagawa (JP); Takao Mandai, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 701 days.

(21) Appl. No.: 16/614,588

(22) PCT Filed: May 17, 2018

(86) PCT No.: PCT/JP2018/019208
§ 371 (c)(1),
(2) Date: Nov. 18, 2019

(87) PCT Pub. No.: WO2018/212312
PCT Pub. Date: Nov. 22, 2018

(65) Prior Publication Data
US 2020/0182850 A1    Jun. 11, 2020

Related U.S. Application Data

(60) Provisional application No. 62/508,609, filed on May 19, 2017.

(51) Int. Cl.
*G01N 33/94* (2006.01)
*A61K 45/06* (2006.01)
*G01N 33/15* (2006.01)

(52) U.S. Cl.
CPC ........... *G01N 33/944* (2013.01); *G01N 33/15* (2013.01); *A61K 45/06* (2013.01); *G01N 2333/4703* (2013.01); *G01N 2500/04* (2013.01); *G01N 2500/20* (2013.01)

(58) Field of Classification Search
CPC ............. G01N 33/944; G01N 33/15; G01N 2333/4703; G01N 2500/04; G01N 2500/20; A61K 45/06; A61P 25/28
See application file for complete search history.

(56) References Cited

U.S. PATENT DOCUMENTS

2005/0096387 A1   5/2005   Verheijen et al.
2016/0326144 A1   11/2016  Groebke Zbinden et al.

FOREIGN PATENT DOCUMENTS

| JP | 2007-509152 A | 4/2007 |
|----|---|---|
| JP | 2017-501233 A | 1/2017 |
| WO | WO-2005/042475 A2 | 5/2005 |
| WO | WO-2010/059773 A1 | 5/2010 |
| WO | WO-2011/049731 A1 | 4/2011 |
| WO | WO-2013/129622 A1 | 9/2013 |
| WO | WO-2014/077401 A1 | 5/2014 |
| WO | WO-2015/110370 A1 | 7/2015 |
| WO | WO-2015/163485 A1 | 10/2015 |
| WO | WO-2015/174534 A1 | 11/2015 |
| WO | WO-2015/190564 A1 | 12/2015 |
| WO | WO-2016/208775 A1 | 12/2016 |
| WO | WO-2017/069173 A1 | 4/2017 |

OTHER PUBLICATIONS

Yeatman et al., J. Biol. Chem., vol. 289, No. 22: 15858-866, May 30, 2014 (Year: 2014).*
Tarr et al., ACS Chemical Neurosci., 3:884-895, 2012 (Year: 2012).*
Avlani et al., Mol Pharmacol., vol. 78, No. 1:94-104, 2010 (Year: 2010).*
Leach et al., Neuropsychopharmacology, vol. 35:855-869, 2010 (Year: 2010).*
Black et al., Proc. R. Soc. London B. Biol. Sci. pp. 141-162, 1983 (Year: 1983).*
Aurelio et al., J Med. Chem., 52(14):4543-4547, 2009 (Year: 2009).*
Canals, M., Lane, J.R., Wen, A., Scammells, P.J., Sexton, P.M. and Christopoulos, A., 2012. A Monod-Wyman-Changeux mechanism can explain G protein-coupled receptor (GPCR) allosteric modulation. Journal of Biological Chemistry, 287(1), pp. 650-659. (Year: 2012).*
Abdul-Ridha et al., "Mechanistic Insights into Allosteric Structure-Function Relationships at the M1 Muscarinic Acetylcholine Receptor," Journal of Biological Chemistry, Oct. 17, 2014, 289(48):33701-33711.
Conn et al., "Opportunities and challenges in the discovery of allosteric modulators of GPCRs for treating CNS disorders," Sep. 1, 2014, 13(9):692-708.
Davoren et al., "Discovery of the Potent and Selective M1 PAM-Agonist N-[(3R,4S)-3-Hydroxytetrahydro-2H-pyran-4-yl}-5-methyl-4-[4-(1,3-thiazol-4-yl)benzyl]pyridine-2-carboxamide (PF-06767832): Evaluation of Efficacy and Cholinergic Side Effects," Journal of Medicinal Chemistry, Jul. 14, 2016, 59(13):6313-6328.
Homsher et al., "High-Throughput Agonist Shift Assay Development for the Analysis of M1-Positive Allosteric Modulators," SLAS Discovery, 2017, 22(8):1060-1066.
Rook et al., "Diverse Effects on M1 Signaling and Adverse Effect Liability within a Series of M1 Ago-PAMs," ACS Chem. Neurosci., 2017 (Dec. 21, 2016), 8(4):866-883.

(Continued)

*Primary Examiner* — Karlheinz R. Skowronek
*Assistant Examiner* — Meredith Abbott Vassell
(74) *Attorney, Agent, or Firm* — Foley & Lardner LLP

(57) ABSTRACT

The present invention provides a useful and efficient screening method for finding a cholinergic muscarinic M1 receptor positive allosteric modulator (M1PAM) with reduced cholinergic side effects. The present invention also provides a method for treating Alzheimer's disease and the like, a method for reducing cholinergic side effects, and the like which use M1PAM selected by the screening method and having a low α value, or the M1PAM and an acetylcholinesterase inhibitor.

12 Claims, 20 Drawing Sheets

Specification includes a Sequence Listing.

(56) References Cited

OTHER PUBLICATIONS

Davie et al., "Synthesis and Pharmacological Evaluation of Analogues of Benzyl Quinolone Carboxylic Acid (BQCA) Designed to Bind Irreversibly to an Allosteric Site of the $M_1$ Muscarinic Acetylcholine Receptor," Journal of Medicinal Chemistry, May 23, 2014, 57(12):5405-5418.

Kimura et al., "In Vitro Characterization of TAK-071: A Novel Muscarinic $M_1$ Receptor-Positive Allosteric Modulator with Low Cooperativity," Alzheimer's Association International Conference, Jul. 17, 2017, p. 2-051 and poster.

Kimura et al., "In vivo characterization of TAK-071, a novel muscarinic $M_1$ receptor positive allosteric modulator," Neuroscience 2017 by Society for Neuroscience, Nov. 12, 2017, and abstract and poster.

Kurimoto et al., "An Approach to Discover Novel Muscarinic $M_1$ Receptor-Positive Allosteric Modulators with Potent Cognitive Improvement and Minimized Gastrointestinal Dysfunction," Alzheimer's Association International Conference, Jul. 17, 2017, p. 2-048 and poster.

Kurimoto et al., "An Approach to Discovering Novel Muscarinic $M_1$ Receptor Positive Allosteric Modulators with Potent Cognitive Improvement and Minimized Gastrointestinal Dysfunction," The Journal of Pharmacology and Experimental Therapeutics, Jan. 2018, 364:28-37.

Kurimoto et al., "TAK-071, a muscarinic $M_1$ receptor positive allosteric modulator, attenuates scopolamine-induced quantitative electroencephalogram power spectral changes in cynomolgus monkeys," PLOS One, Mar. 11, 2019, 14(3):e0207969, 15 pages.

Kurimoto et al., "TAK-071, a novel muscarinic $M_1$ receptor positive allosteric modulator, regulates quantitative electroencephalogram power spectra in scopolamine challenge paradigm," Neuroscience 2017 by Society for Neuroscience, Nov. 12, 2017, abstract and poster.

Mandai et al., "In Vivo Pharmacological Comparison of TAK-071, a Positive Allosteric Modulator of Muscarinic $M_1$ Receptor, and Xanomeline, an Agonist of Muscarinic $M_1/M_4$ Receptor, in Rodents," Neuroscience, 2019, 414:60-76.

Mandai et al., "TAK-071, a positive allosteric modulator of $M_1$ muscarinic acetylcholine receptor, induces a C-Fos expression pattern similar to that by xanomeline in mouse brain," Neuroscience 2017 by Society for Neuroscience, Nov. 12, 2017, abstract and poster.

Sako et al., "TAK-071, a novel $M_1$ positive allosteric modulator with low cooperativity, improves cognitive function in rodents with few cholinergic side effects," Neuropsychopharmacology, 2019, 44:950-960.

Wess et al., "Muscarinic acetylcholine receptors: mutant mice provide new insights for drug development," Nature Reviews Drug Discovery, Sep. 2007, 6:721-733.

\* cited by examiner

Fig. 2A-2C
FIG. 2A
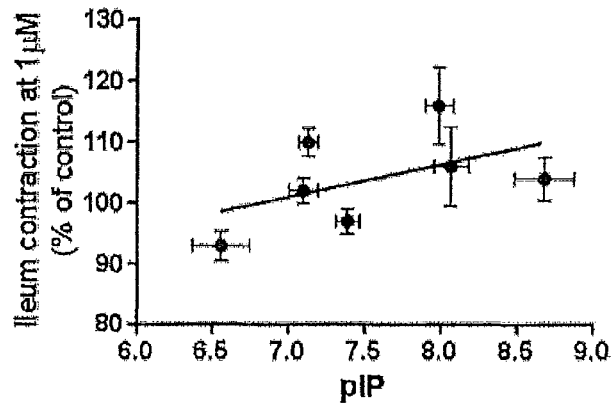
FIG. 2B
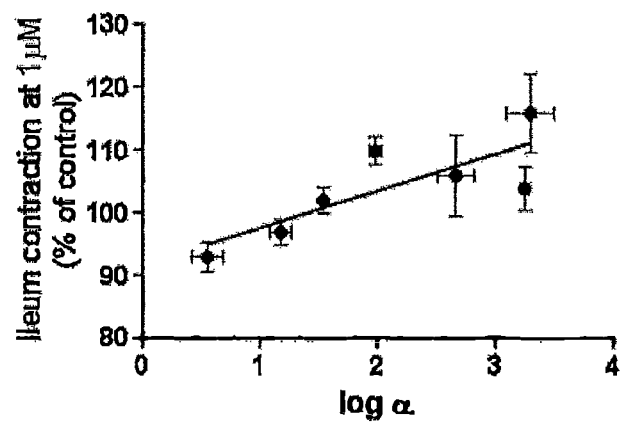
FIG. 2C
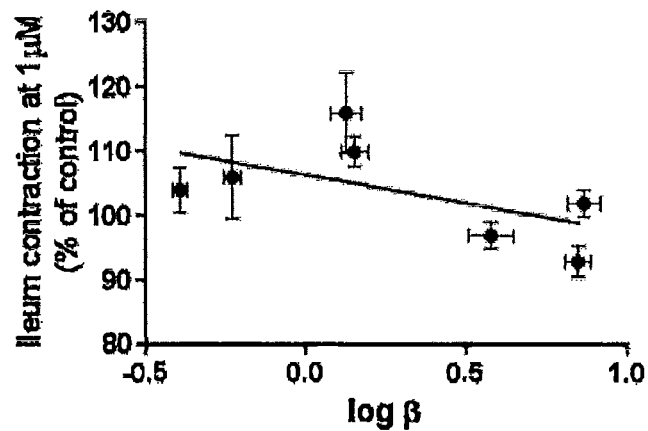

Fig. 3-A
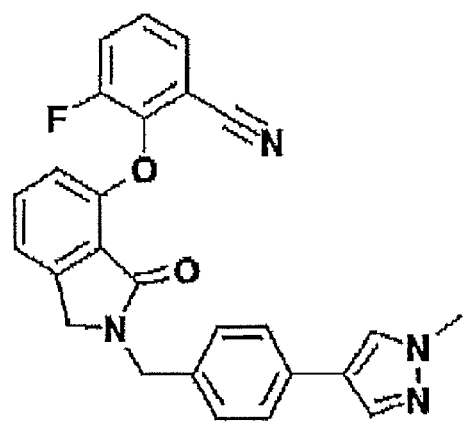
Fig. 3-B
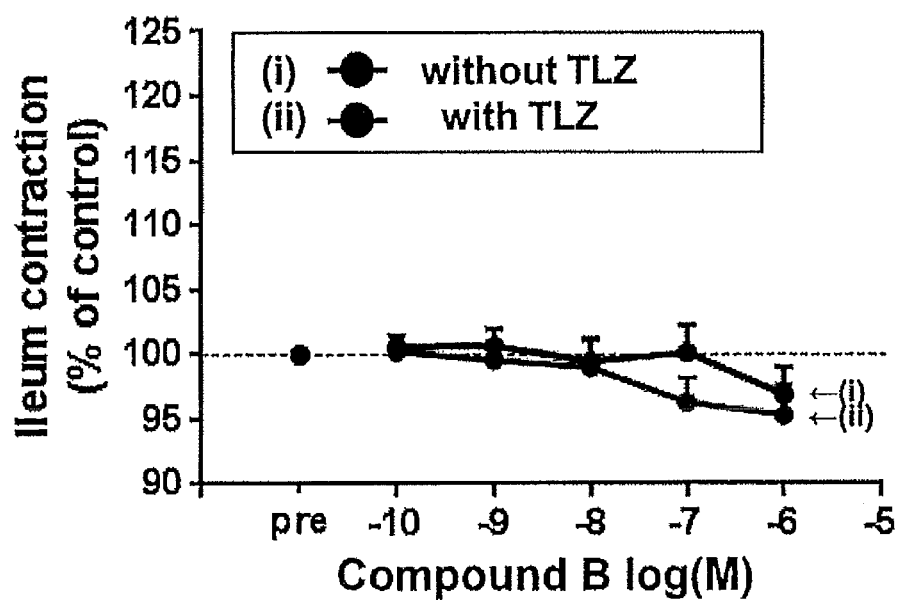

Fig. 3-C
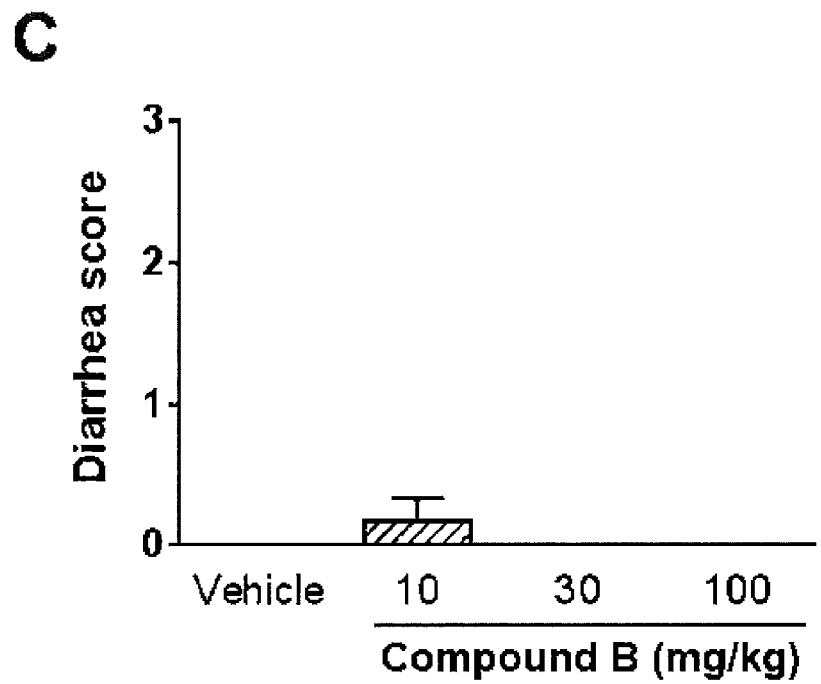
Fig. 3-D
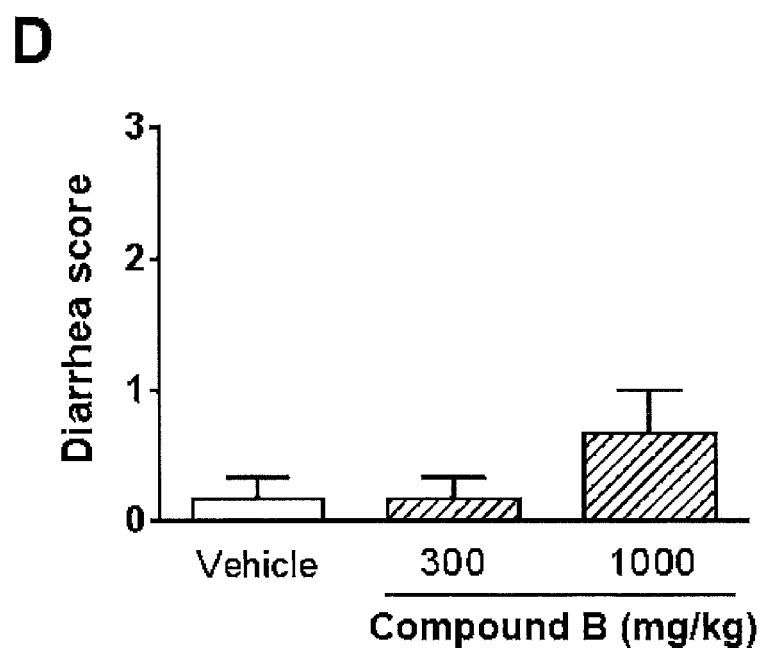

Fig. 3-E
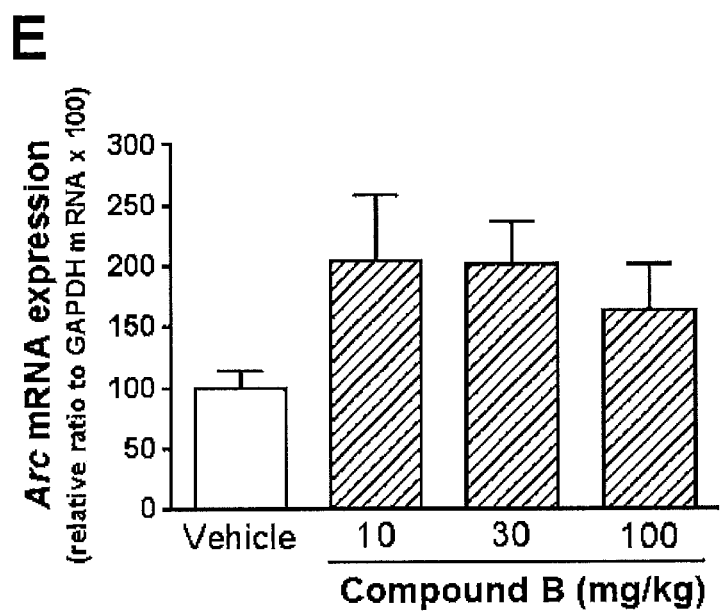
Fig. 3-F
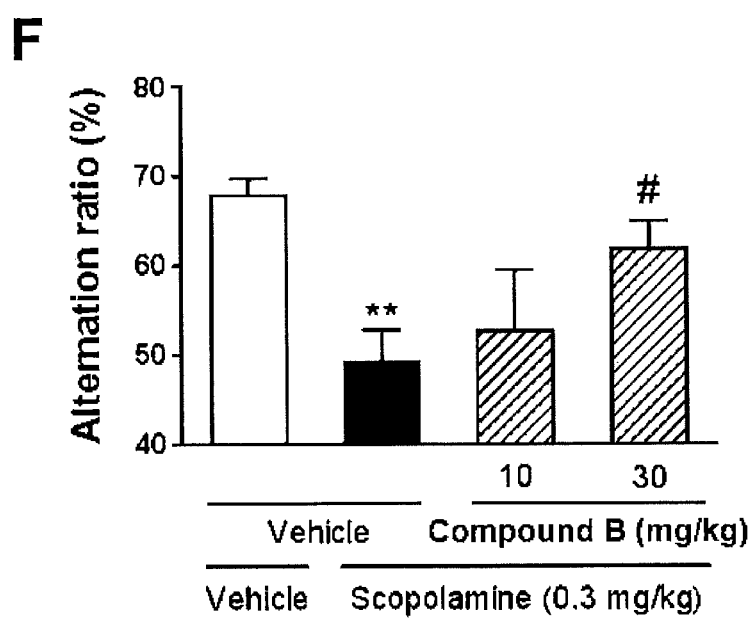

Fig. 4-A
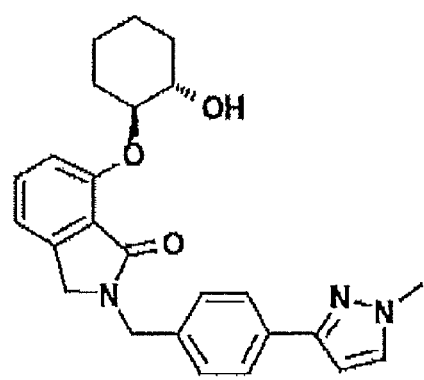
Fig. 4-B
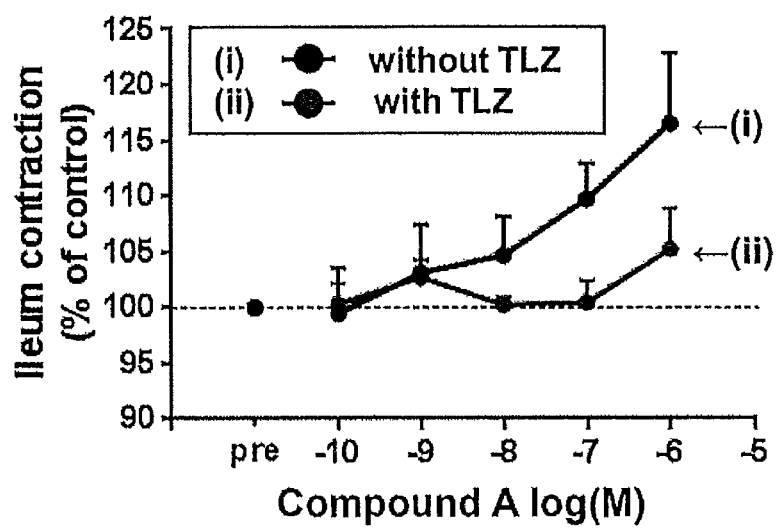

Fig. 4-C
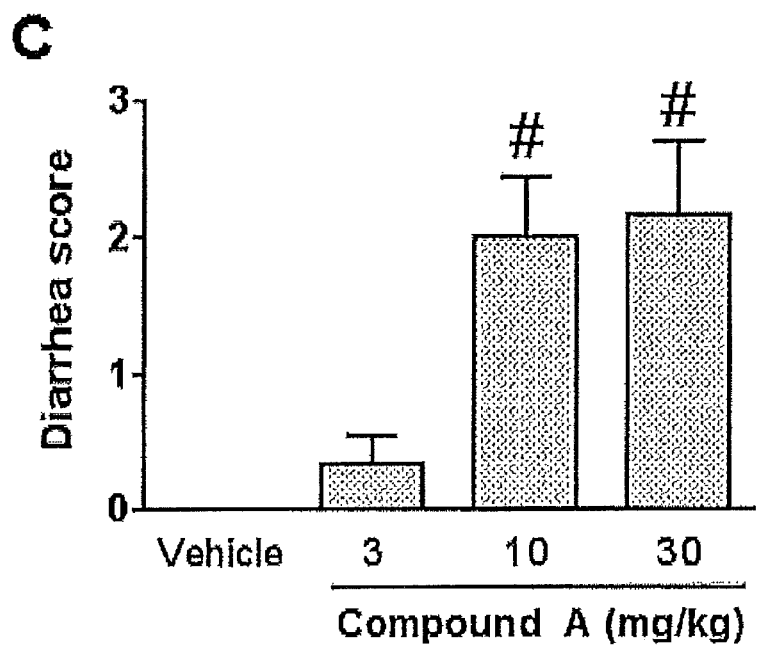
Fig. 4-D
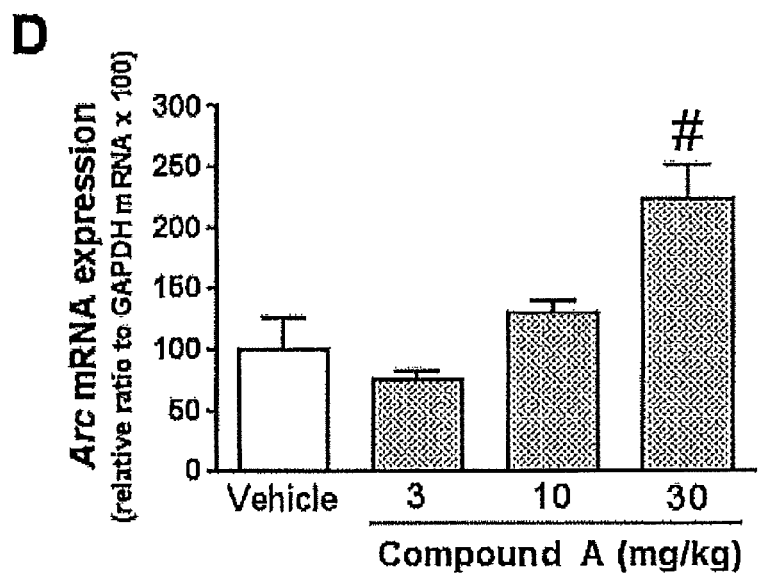

Fig. 4-E
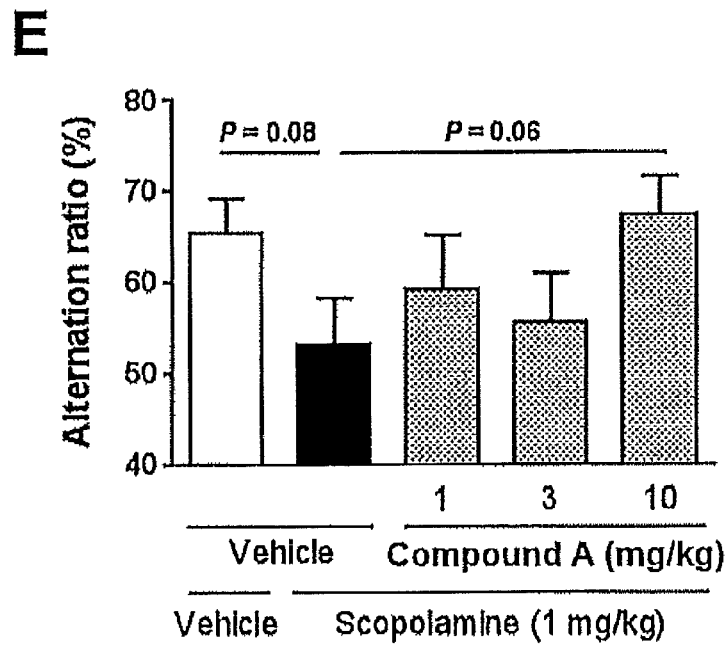
Fig. 4-F
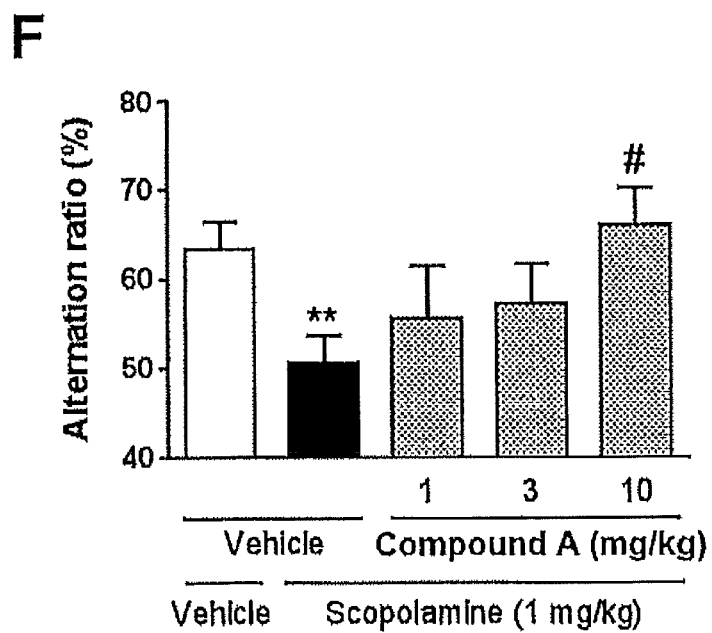

Fig 5A-5C
FIG. 5A
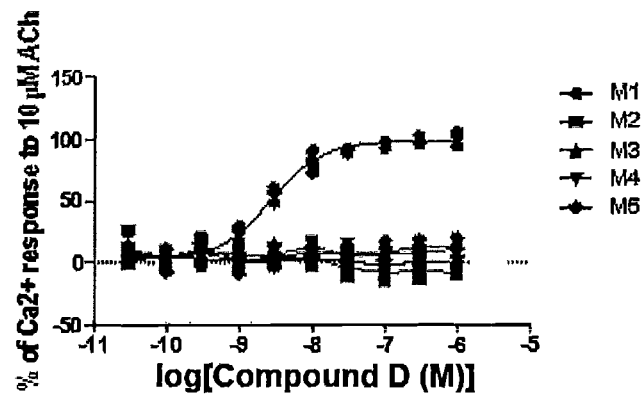
FIG. 5B
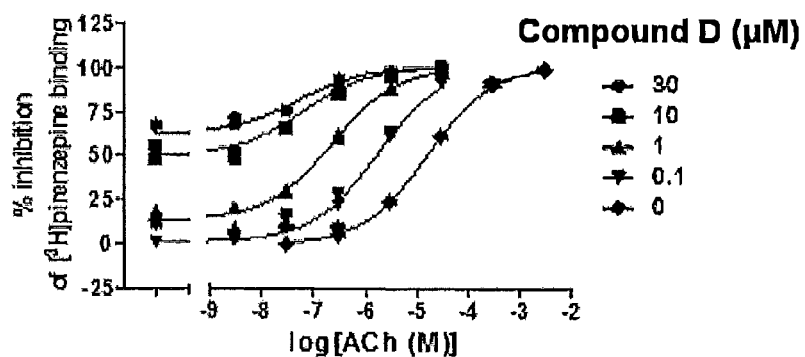
FIG. 5C
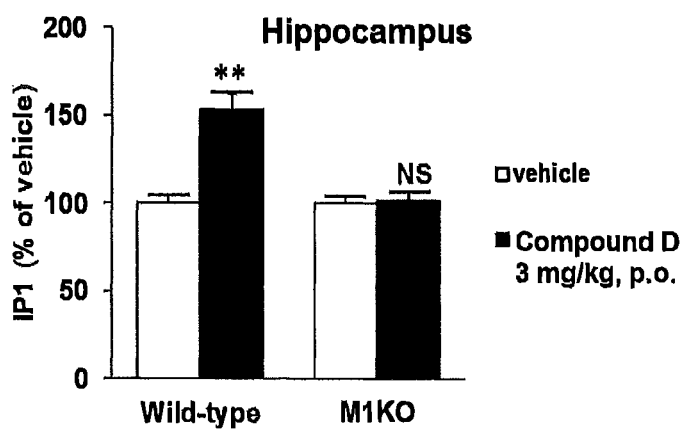

Fig. 6A-6D
FIG. 6A
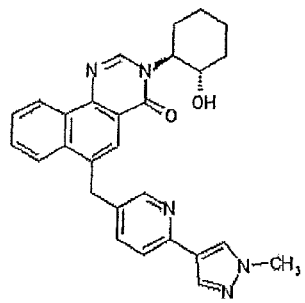
FIG. 6B
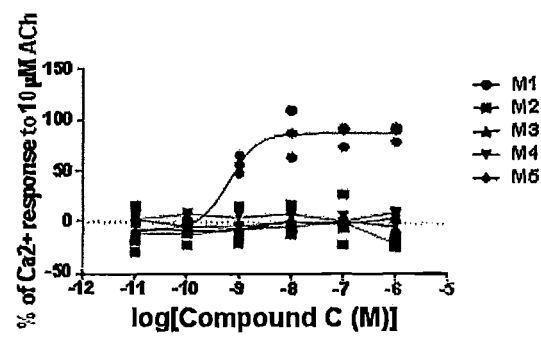
FIG. 6C
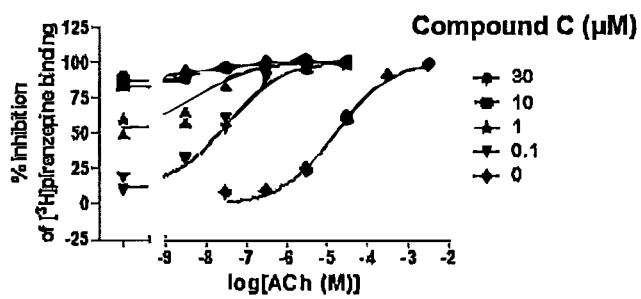
FIG. 6D
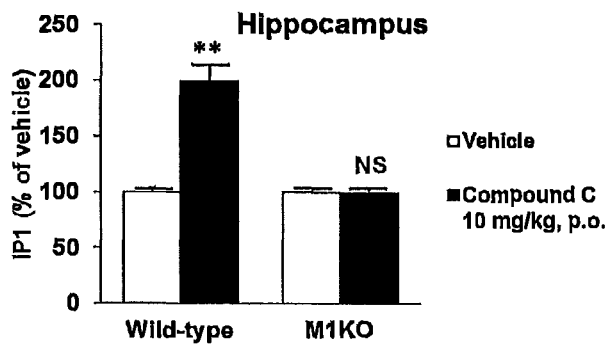

Fig. 7
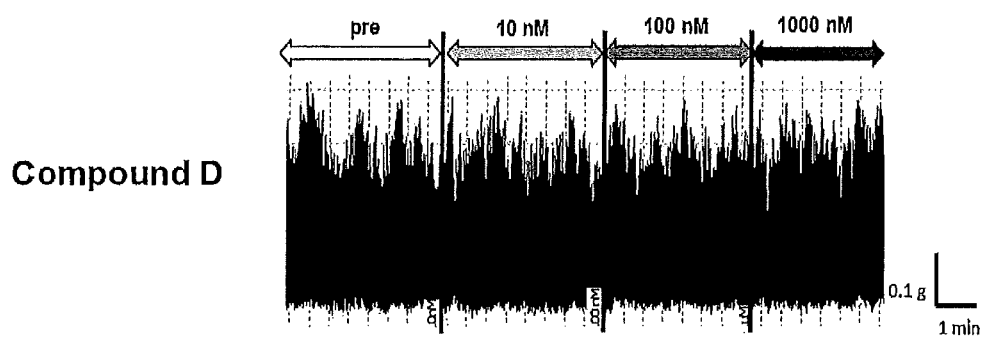
Compound D
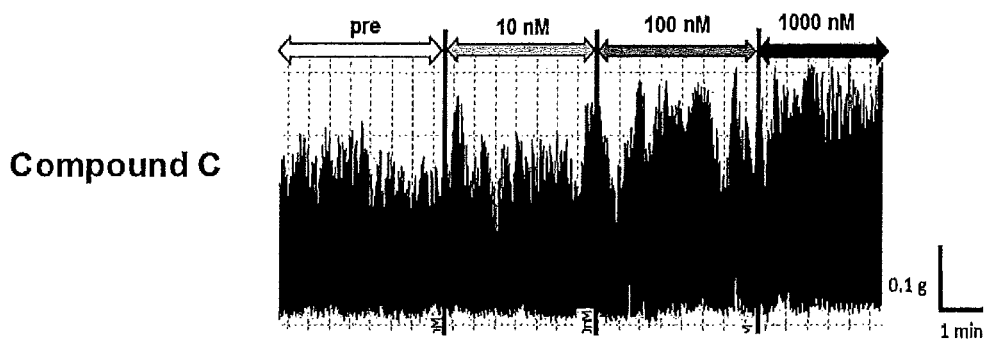
Compound C
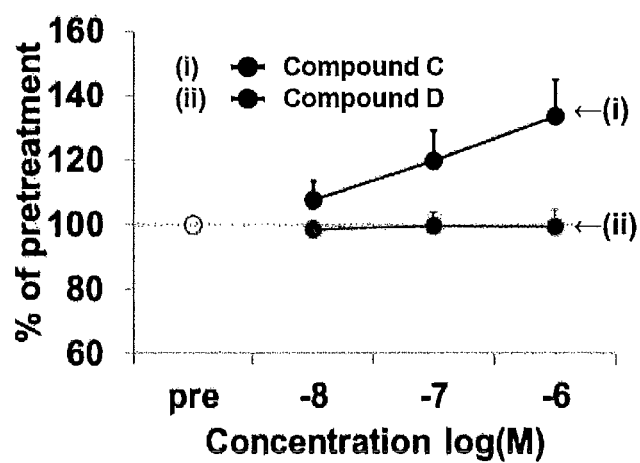

Fig. 8A-8D
FIG. 8A
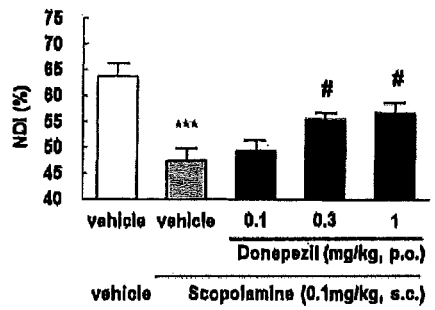
FIG. 8B
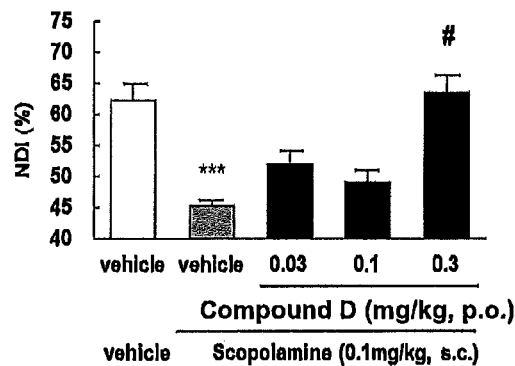
FIG. 8C
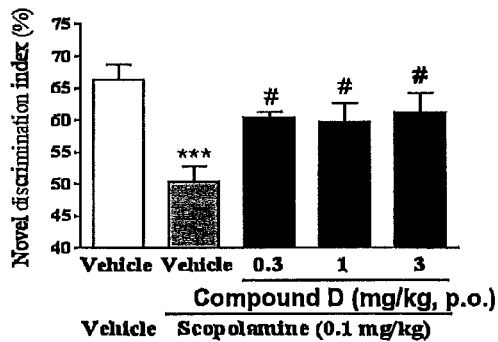
FIG. 8D
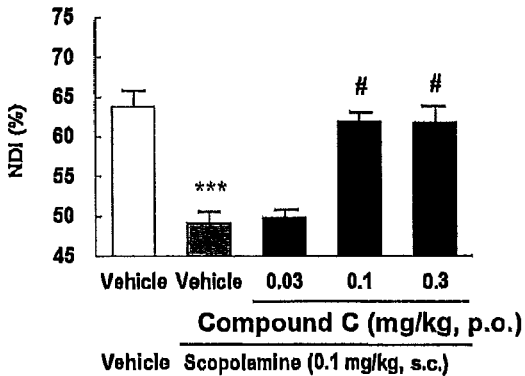

Fig. 9A-9C
FIG. 9A
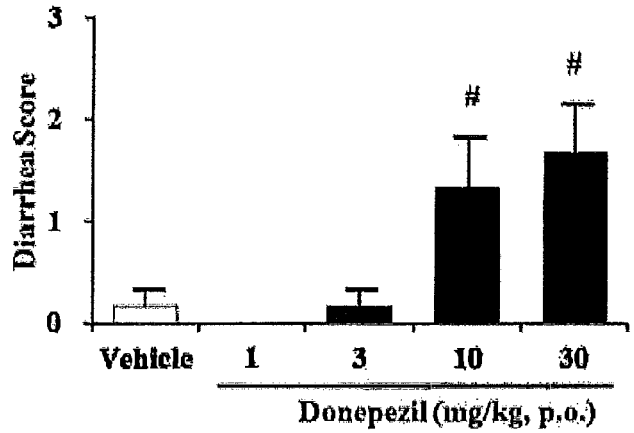
FIG. 9B
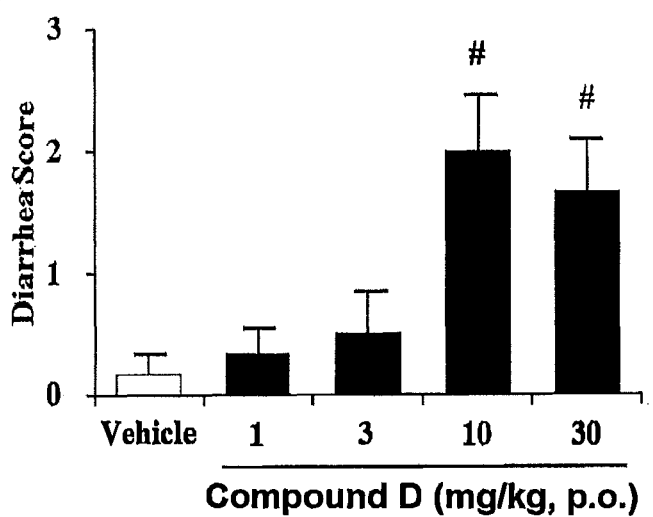
FIG. 9C
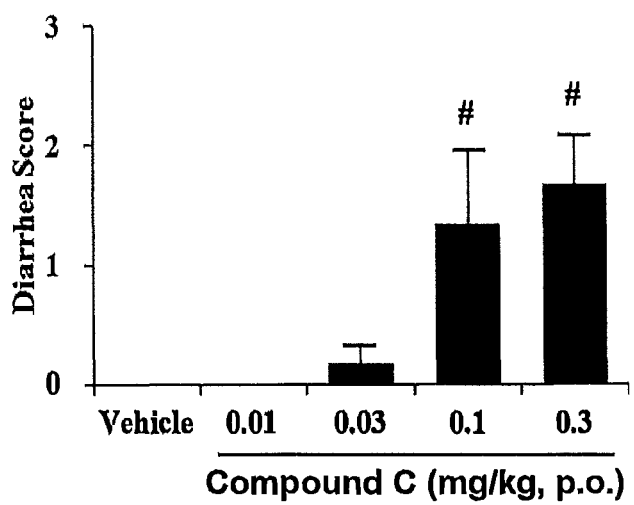

Fig. 10A-10B
FIG. 10A
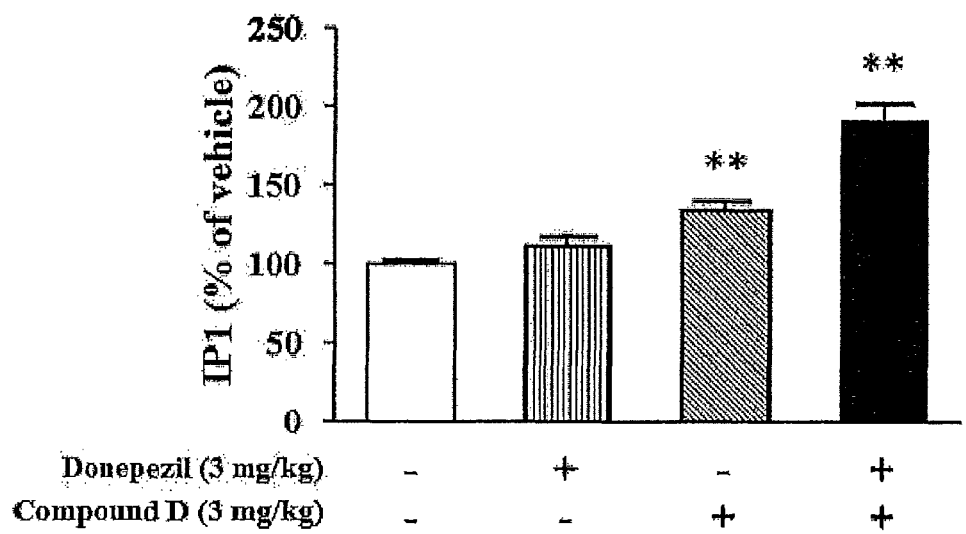
FIG. 10B
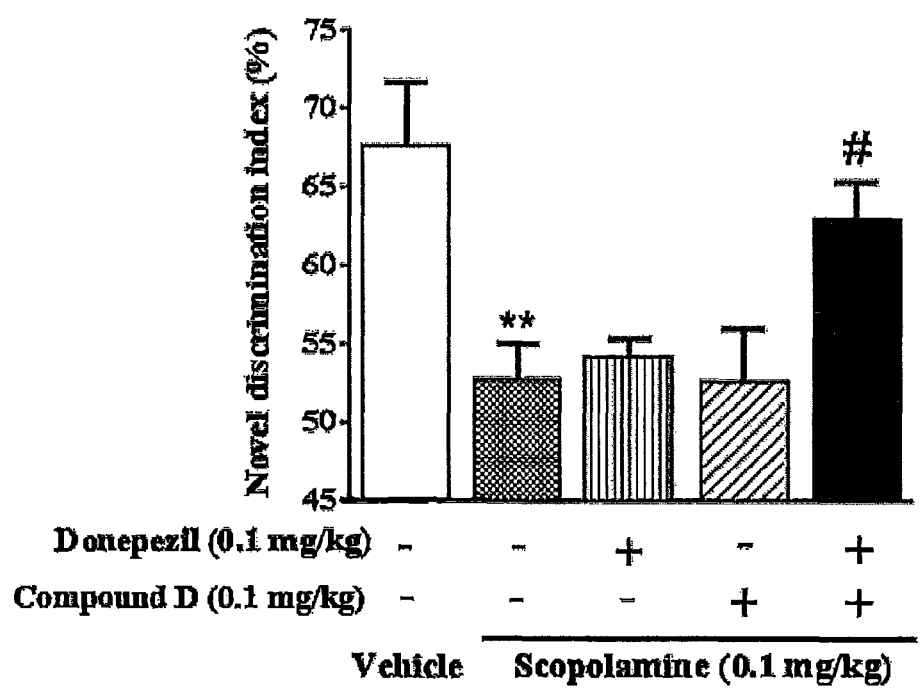

Fig. 12
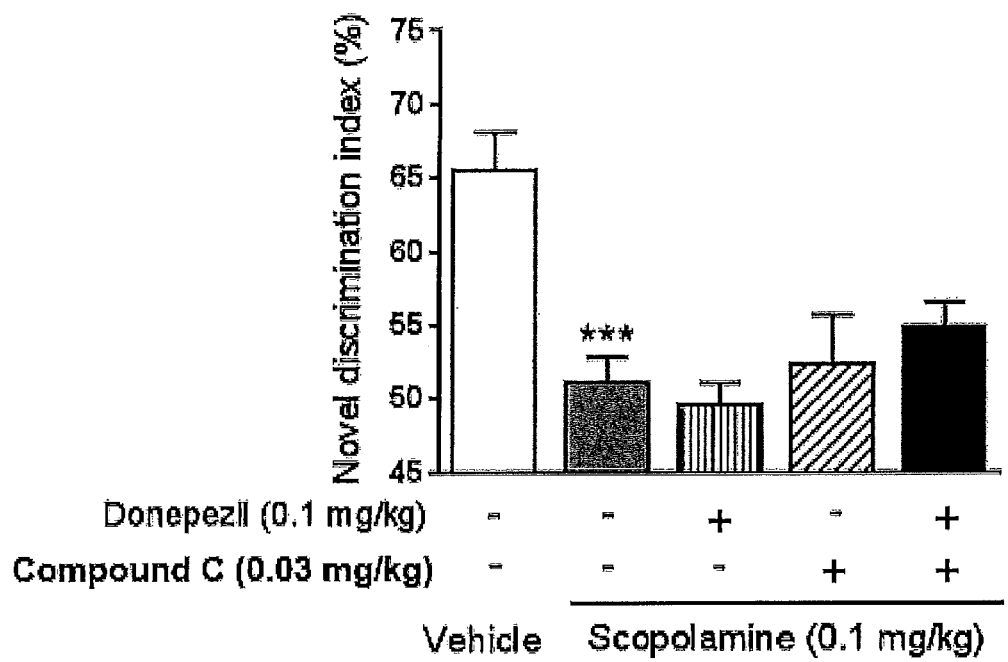
Fig. 13-A
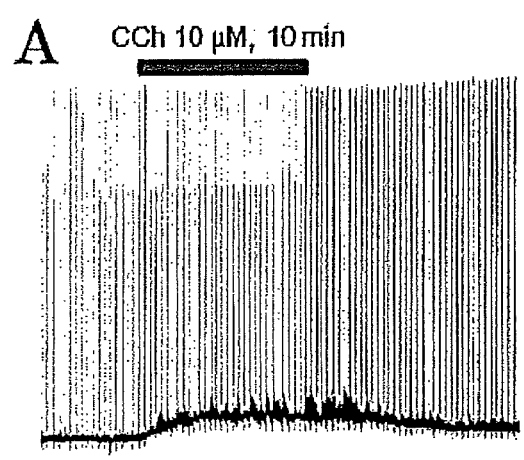

Fig. 13-B
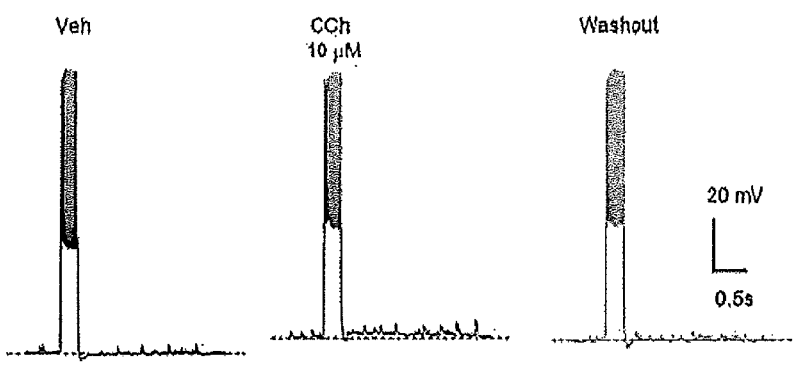
Fig. 13-C
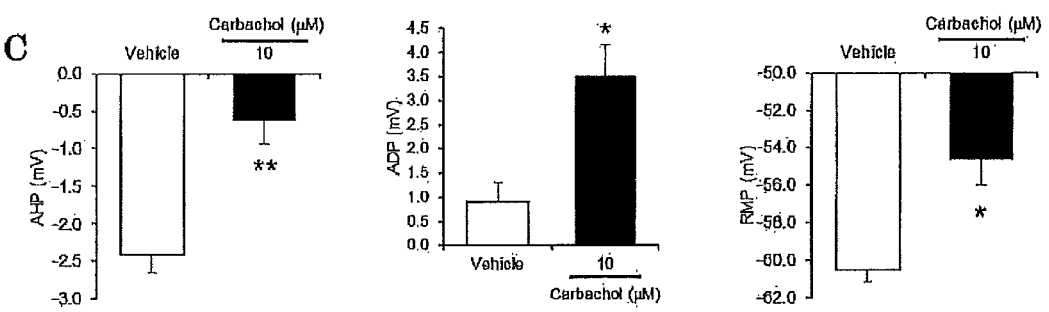
Fig. 13-D
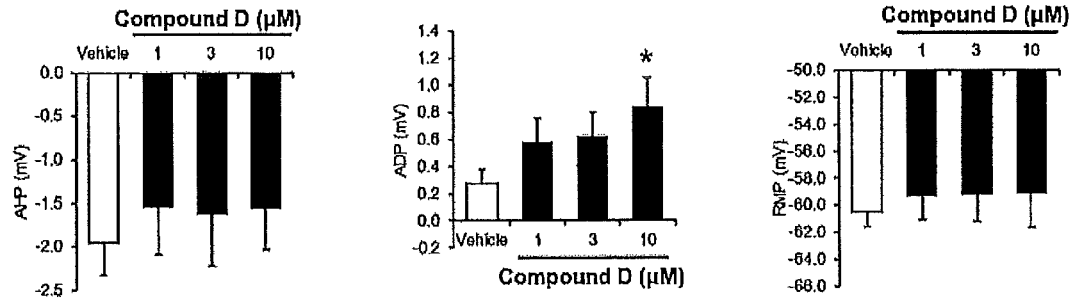

Fig. 13-E
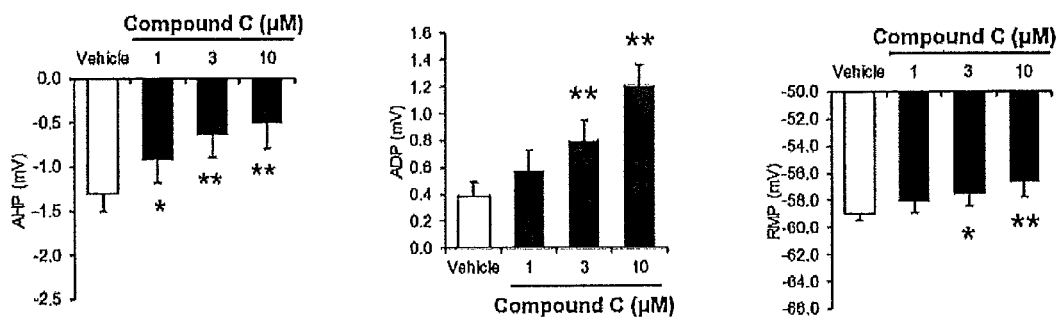
Fig. 14
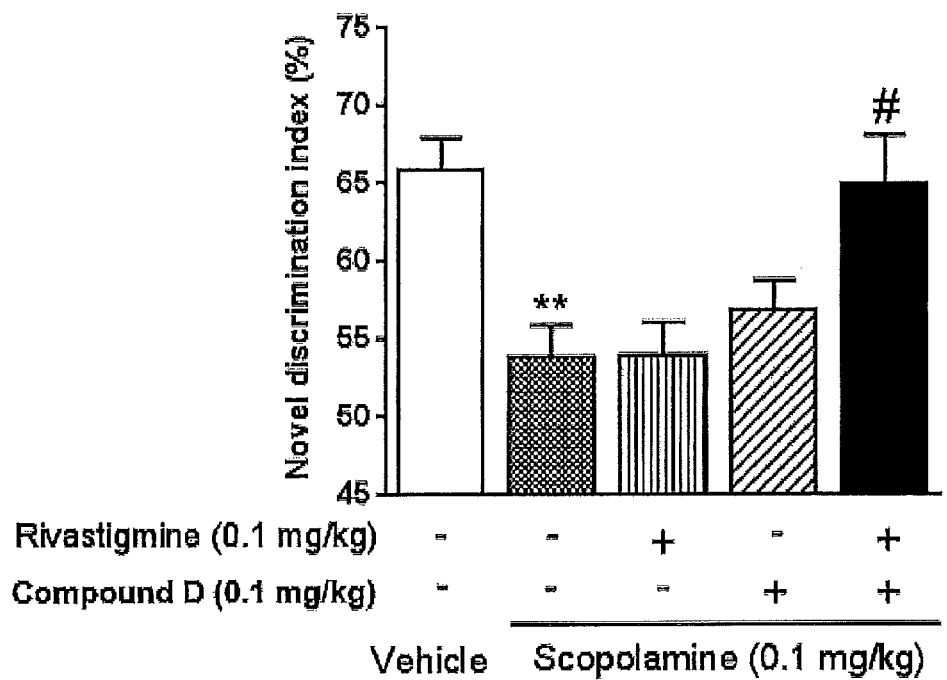

Fig. 15

Human M1R nucleic acid (SEQ ID No:1)

ATGAACACTTCAGCCCCACCTGCTGTCAGCCCCAACATCACCGTCCTGGCACCAGGAAAGGGTCCCTGGC
AAGTGGCCTTCATTGGGATCACCACGGGCCTCCTGTCGCTAGCCACAGTGACAGGCAACCTGCTGGTACT
CATCTCTTTCAAGGTCAACACGGAGCTCAAGACAGTCAATAACTACTTCCTGCTGAGCCTGGCCTGTGCT
GACCTCATCATCGGTACCTTCTCCATGAACCTCTATACCACGTACCTGCTCATGGGCCACTGGGCTCTGG
GCACGCTGGCTTGTGACCTCTGGCTGGCCCTGGACTATGTGGCCAGCAATGCCTCCGTCATGAATCTGCT
GCTCATCAGCTTTGACCGCTACTTCTCCGTGACTCGGCCCCTGAGCTACCGTGCCAAGCGCACACCCCGC
CGGGCAGCTCTGATGATCGGCCTGGCCTGGCTGGTTTCCTTTGTGCTCTGGGCCCCAGCCATCCTCTTCT
GGCAGTACCTGGTAGGGGAGCGGACAGTGCTAGCTGGGCAGTGCTACATCCAGTTCCTCTCCCAGCCCAT
CATCACCTTTGGCACAGCCATGGCTGCCTTCTACCTCCCTGTCACAGTCATGTGCACGCTCTACTGGCGC
ATCTACCGGGAGACAGAGAACCGAGCACGGGAGCTGGCAGCCCTTCAGGGCTCCGAGACGCCAGGCAAAG
GGGGTGGCAGCAGCAGCAGCTCAGAGAGGTCTCAGCCAGGGGCTGAGGGCTCACCAGAGACTCCTCCAGG
CCGCTGCTGTCGCTGCTGCCGGGCCCCCAGGCTGCTGCAGGCCTACAGCTGGAAGGAAGAAGAGGAAGAG
GACGAAGGCTCCATGGAGTCCCTCACATCCTCAGAGGGAGAGGAGCCTGGCTCCGAAGTGGTGATCAAGA
TGCCAATGGTGGACCCCGAGGCACAGGCCCCCACCAAGCAGCCCCCACGGAGCTCCCCAAATACAGTCAA
GAGGCCGACTAAGAAAGGGCGTGATCGAGCTGGCAAGGGCCAGAAGCCCCGTGGAAAGGAGCAGCTGGCC
AAGCGGAAGACCTTCTCGCTGGTCAAGGAGAAGAAGGCGGCTCGGACCCTGAGTGCCATCCTCCTGGCCT
TCATCCTCACCTGGACACCGTACAACATCATGGTGCTGGTGTCCACCTTCTGCAAGGACTGTGTTCCCGA
GACCCTGTGGGAGCTGGGCTACTGGCTGTGCTACGTCAACAGCACCATCAACCCCATGTGCTACGCACTC
TGCAACAAAGCCTTCCGGGACACCTTTCGCCTGCTGCTGCTTTGCCGCTGGGACAAGAGACGCTGGCGCA
AGATCCCCAAGCGCCCTGGCTCCGTGCACCGCACTCCCTCCCGCCAATGCTGA

Fig. 16

Human M1R protein (SEQ ID No:2)

```
  1 mntsappavs pnitvlapgk gpwqvafigi ttgllslatv tgnllvlisf kvntelktvn
 61 nyfllslaca dliigtfsmn lyttyllmgh walgtlacdl wlaldyvasn asvmnlllis
121 fdryfsvtrp lsyrakrtpr raalmiglaw lvsfvlwapa ilfwqylvge rtvlagqcyi
181 qflsqpiitf gtamaafylp vtvmctlywr iyretenrar elaalqgset pgkgggssss
241 sersqpgaeg spetppgrcc rccraprllq ayswkeeeee degsmeslts segeepgsev
301 vikmpmvdpe aqaptkqppr sspntvkrpt kkgrdragkg qkprgkeqla krktfslvke
361 kkaartlsai llafiltwtp ynimvlvstf ckdcvpetlw elgywlcyvn stinpmcyal
421 cnkafrdtfr llllcrwdkr rwrkipkrpg svhrtpsrqc
```

METHOD FOR MEASURING ALPHA VALUE OF MUSCARINIC M1 RECEPTOR POSITIVE ALLOSTERIC MODULATORS

CROSS-REFERENCE TO RELATED APPLICATIONS

This application is the U.S. National Stage of PCT/JP2018/019208, filed May 17, 2018, which claims priority to U.S. Provisional Application No. 62/508,609, filed May 19, 2017.

The instant application contains a Sequence Listing which has been submitted in ASCII format via EFS-WEB and is hereby incorporated by reference in its entirety. Said ASCII copy, created on Nov. 15, 2019, is named sequence.txt and is 11,535 bytes.

TECHNICAL FIELD

The present invention relates to a useful and efficient screening method for finding a cholinergic muscarinic M1 receptor positive allosteric modulator (M1PAM) with reduced cholinergic side effects. The present invention also relates to a method for treating Alzheimer's disease and the like, a for reducing cholinergic side effects, and the like which use M1PAM having a low α value, or the M1PAM and an acetylcholinesterase inhibitor. Here, the positive allosteric modulator has an action of enhancing the receptor function by binding to a site different from the endogenous activator (acetylcholine (ACh) in cholinergic muscarinic M1 receptor).

BACKGROUND ART

Background of the Invention

ACh is a neurotransmitter that induces signal transduction in the central nervous system and neuromuscular junction (parasympathetic nerve and motor nerve). In the central nervous system, the nuclei of origin of acetylcholine neuron are in the brain stem and forebrain, and the acetylcholine neuron projects to the cerebral cortex, hippocampus and limbic areas. Furthermore, some interneurons in certain brain regions such as corpus striatum and the like use ACh as a neurotransmitter. Acetylcholine receptors are classified into ligand-gated ion channels (cholinergic nicotinic receptors) and G protein-coupled receptors (cholinergic muscarinic receptors). The cholinergic muscarinic receptor is one type of the receptors for ACh and was named based on the selective activation of the receptor by muscarine. Muscarinic receptors are further classified into subtypes M1 to M5, and cholinergic muscarinic M1 receptors (M1Rs) are widely distributed mainly in the brain and are known to be particularly deeply involved in learning, memory, sleep, and the like. The importance of M1R in brain physiology is well known, and a compound having an M1R function enhancing action is expected to be useful as an agent for preventing or treating psychiatric diseases, neurodegenerative diseases, memory disorders, pain, sleep disorders, Parkinson's disease with dementia, dementia with Lewy bodies and the like (non-patent document 1).

Patent document 1 discloses the following compound as a compound having M1PAM activity and useful for the treatment of Alzheimer's disease, schizophrenia, pain, sleep disorder and the like.

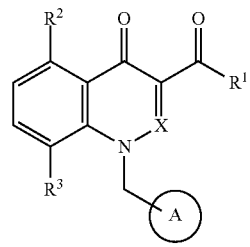

wherein each symbol is as defined in the document.

Patent document 2 discloses the following compound as a compound having M1PAM activity and useful for the treatment of Alzheimer's disease, schizophrenia, pain, sleep disorder and the like.

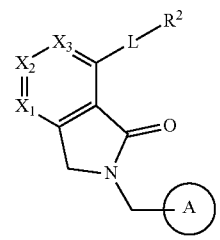

wherein each symbol is as defined in the document.

Patent document 3 discloses the following compound as a compound having M1PAM activity and useful for the treatment of Alzheimer's disease, schizophrenia, pain, sleep disorder, Parkinson's disease with dementia, dementia with Lewy Bodies and the like.

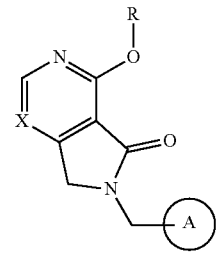

wherein each symbol is as defined in the document.

Patent document 4 discloses the following compound as a compound having M1PAM activity and useful for the treatment of Alzheimer's disease, schizophrenia, pain, sleep disorder, Parkinson's disease with dementia, dementia with Lewy Bodies and the like.

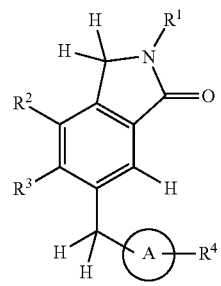

wherein each symbol is as defined in the document.

Patent document 5 discloses the following compound as a compound having M1PAM activity and useful for the treatment of Alzheimer's disease, schizophrenia, pain, sleep disorder, Parkinson's disease with dementia, dementia with Lewy Bodies and the like.

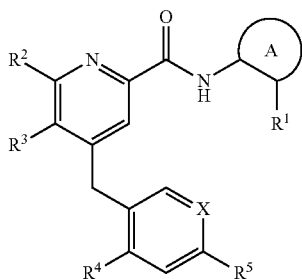

wherein each symbol is as defined in the document.

Patent document 6 discloses the following compound as a compound having M1PAM activity and useful for the treatment of Alzheimer's disease, schizophrenia, pain, sleep disorder, Parkinson's disease with dementia, dementia with Lewy Bodies and the like.

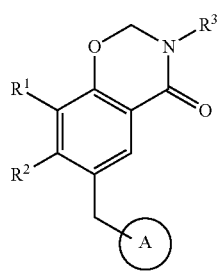

wherein each symbol is as defined in the document.

Patent document 7 discloses the following compound as a compound having M1PAM activity and useful for the treatment of Alzheimer's disease, schizophrenia, pain, sleep disorder, Parkinson's disease with dementia, dementia with Lewy Bodies and the like.

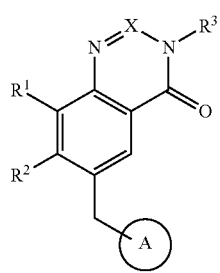

wherein each symbol is as defined in the document.

Patent document 8 discloses the following compound as a compound having M1PAM activity and useful for the treatment of Alzheimer's disease, schizophrenia, pain, sleep disorder, Parkinson's disease with dementia, dementia with Lewy Bodies and the like.

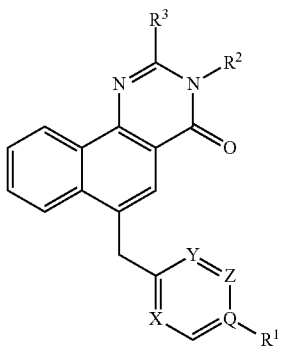

wherein each symbol is as defined in the document.

DOCUMENT LIST

Patent Documents patent document 1: WO 2013/129622
patent document 2: WO 2014/077401
patent document 3: WO 2015/174534
patent document 4: WO 2015/163485
patent document 5: WO 2015/190564
patent document 6: WO 2016/208775
patent document 7: WO 2017/069173
patent document 8: WO 2010/059773

Non-Patent Document non-patent document 1: Nature Reviews Drug Discovery, 2007, 6, 721-733.

SUMMARY OF THE INVENTION

Problems to be Solved by the Invention

The present invention aims to find side effects that can be caused by cholinergic muscarinic M1 receptor positive allosteric modulator (sometimes to be abbreviated as "M1PAM" in the present DESCRIPTION) from the aspect of improving quality of life (QOL) and the like, and provide a useful and efficient screening method for creating M1PAM free of the side effects.

Also, the present invention aims to provide a method for treating Alzheimer's disease and the like and a method for reducing cholinergic side effects which use M1PAM having a low α value.

Furthermore, the present invention aims to provide a method for treating Alzheimer's disease and the like and a method for reducing cholinergic side effects which use M1PAM having a low α value, an acetylcholinesterase inhibitor and the like.

Means of Solving the Problems

The present inventors have conducted intensive studies in an attempt to solve the aforementioned problems and found firstly that cholinergic side effects such as diarrhea and the like appear via cholinergic muscarinic M1 receptor (sometimes to be abbreviated as "M1R" in the present DESCRIPTION). Next, the present inventors evaluated various M1PAMs to find a positive correlation between the α value of M1PAM and the contraction strength of ileum by electric field stimulation. Furthermore, the present inventors have also found that a combination therapy of the above-mentioned M1PAM having a low α value and an acetylcholinesterase inhibitor affords unexpectedly superior therapeutic effects on Alzheimer's disease and the like as compared to monotherapy with each compound. Based on these findings, the present inventors have conducted further studies and completed the present invention.

Therefore, the present invention provides the following.

[1] A method for screening for a cholinergic muscarinic M1 receptor positive allosteric modulator with reduced cholinergic side effects, comprising using an α-value as an index.

[2] A method for treating Alzheimer's disease, schizophrenia, Parkinson's disease with dementia or dementia with Lewy bodies and reducing cholinergic side effects in a mammal, comprising administering an effective amount of a cholinergic muscarinic M1 receptor positive allosteric modulator having a low α-value to the mammal.

[2-1] The method of [2], further comprising monitoring and scoring a severity of the side effects in the mammal after the administration.

[3] The method of [2], wherein the mammal has a cholinergic disorder.

[4] A method for treating Alzheimer's disease, schizophrenia, Parkinson's disease with dementia or dementia with Lewy bodies in a mammal, comprising administering an effective amount of M1PAM having a low α-value to the mammal, wherein the mammal is suffering from a cholinergic side effect caused by an acetylcholinesterase inhibitor.

[5] A method for treating Alzheimer's disease, schizophrenia, Parkinson's disease with dementia or dementia with Lewy bodies and reducing cholinergic side effects in a mammal, comprising administering an effective amount of an acetylcholinesterase inhibitor and then M1PAM having a low α-value to the mammal.

[6] A method for treating Alzheimer's disease, schizophrenia, Parkinson's disease with dementia or dementia with Lewy bodies and reducing cholinergic side effects in a mammal, comprising:
(i) administering an acetylcholinesterase inhibitor to the mammal to cause a side effect, and
(ii) administering an effective amount of M1PAM having a low α-value to the mammal of (i).

[7] A method for reducing an amount of an acetylcholinesterase inhibitor to be administered to a mammal, comprising administering an effective amount of M1PAM having a low α-value to the mammal.

BRIEF DESCRIPTION OF THE DRAWINGS

FIG. 2A-2C depicts relationship between the ileum contraction and MIPAM parameters (Example 12). Scatter plots showing the correlation between the potentiation of ileum contraction and (FIG. 2A) pIP value, an MIPAM activity, (FIG. 2B) log α, a parameter associated with the binding cooperativity between ACh and PAM, or (FIG. 2C) log β, a parameter associated with the magnitude of the allosteric effect of PAM on the signaling efficacy of ACh. Results represent the mean±S.E.M. n=3-11 per group. Parameters used for this figure were shown in Table 1 and 2 in Example 12. The r (correlation coefficient) and p values were calculated by Pearson's correlation test. IP indicates an inflection point.

FIG. 3 depicts effect of a low α-value compound (Compound B) on cognition and diarrhea in mice (Example 13). (A) Chemical structure of Compound B.

FIG. 3 depicts effect of a low α-value compound (Compound B) on cognition and diarrhea in mice (Example 13). (B) The augmentation of ileum contraction by Compound B treatment (0.1 nM-10 µM) in isolated mouse ileum with EFS. TLZ means 1 nM telenzepine pretreatment. Results represent the mean±S.E.M. n=7 per group.

FIG. 3 depicts effect of a low α-value compound (Compound B) on cognition and diarrhea in mice (Example 13). (C) Diarrhea induction by oral treatment of Compound B (10-1000 mg/kg). Results represent the mean±S.E.M. n=6 per group.

FIG. 3 depicts effect of a low α-value compound (Compound B) on cognition and diarrhea in mice (Example 13). (D) Diarrhea induction by oral treatment of Compound B (10-1000 mg/kg). Results represent the mean±S.E.M. n=6 per group.

FIG. 3 depicts effect of a low α-value compound (Compound B) on cognition and diarrhea in mice (Example 13). (E) The change of Arc mRNA expression level in mouse hippocampus by oral treatment of Compound B (10-100 mg/kg) at 90 min after treatment was detected by TaqMan PCR. Results represent the mean±S.E.M. n=5-6 per group.

FIG. 3 depicts effect of a low α-value compound (Compound B) on cognition and diarrhea in mice (Example 13). (F) Effects of Compound B on scopolamine-induced decrease in spontaneous alternation ratio during 5 min measurement in Y-maze task. Compound B was administered orally at 60 min prior to the testing, and scopolamine was treated subcutaneously at 30 min before the testing. Results represent the mean±S.E.M. n=11 per group. **:$P \leq 0.01$ versus control group by Aspin-Welch's t-test. #:$P \leq 0.05$ versus scopolamine-treated group by two-tailed Shirley-Williams test.

FIG. 4 depicts effect of a high α-value compound (Compound A) on cognition and diarrhea in mice (Example 14). (A) Chemical structure of Compound A.

FIG. 4 depicts effect of a high α-value compound (Compound A) on cognition and diarrhea in mice (Example 14). (B) The augmentation of ileum contraction by Compound A treatment (0.1 nM-1 µM) in the isolated mouse ileum with EFS. TLZ means 1 nM telenzepine pretreatment. Results represent the mean±S.E.M. n=3-4 per group.

FIG. 4 depicts effect of a high α-value compound (Compound A) on cognition and diarrhea in mice (Example 14). (C) Diarrhea induction by oral treatment of Compound A (3-30 mg/kg). Results represent the mean±S.E.M. n=6 per group. #:$P \leq 0.05$ versus control group by two-tailed Williams' test.

FIG. 4 depicts effect of a high α-value compound (Compound A) on cognition and diarrhea in mice (Example 14). (D) The change of Arc mRNA expression level in mouse hippocampus by oral administration of Compound A (3-30 mg/kg) at 90 min after treatment was detected by TaqMan PCR. Results represent the mean±S.E.M. n=6 per group. #:P≤0.05 versus control group by two-tailed Shirley-Williams test.

FIG. 4 depicts effect of a high α-value compound (Compound A) on cognition and diarrhea in mice (Example 14). (E) Effect of Compound A on scopolamine-induced decrease in spontaneous alternation ratio in Y-maze task under the conditions of measurement recorded for 5 min. Compound A was administered orally at 60 min prior to the testing, and scopolamine was treated subcutaneously at 30 min before the testing. Results represent the mean±S.E.M. n=7-8 per group. **:P<0.01 versus control group by Aspin-Welch's t-test. #:P<0.05 versus scopolamine-treated group by two-tailed Williams' test. P=0.08 versus vehicle-treated group by Aspin-Welch's t-test. P=0.06 versus scopolamine-treated group by two-tailed Williams' test.

FIG. 4 depicts effect of a high α-value compound (Compound A) on cognition and diarrhea in mice (Example 14). (F) Effect of Compound A on scopolamine-induced decrease in spontaneous alternation ratio in Y-maze task under the conditions of measurement recorded for 8 min. Compound A was administered orally at 60 min prior to the testing, and scopolamine was treated subcutaneously at 30 min before the testing. Results represent the mean±S.E.M. n=7-8 per group. **:P≤0.01 versus control group by Aspin-Welch's t-test. #:P≤ 0.05 versus scopolamine-treated group by two-tailed Williams' test. P=0.08 versus vehicle-treated group by Aspin-Welch's t-test. P=0.06 versus scopolamine-treated group by two-tailed Williams' test.

FIG. 5A-5C depicts Compound D selectively activates human M1R with low α-value of 199 in vitro and in vivo (Example 23). FIG. 5A, Effects of Compound D on $Ca^{2+}$ response in CHO-K1 cells expressing human M1-5R. The data is expressed as a percentage when the response activity to 10 μM ACh is 100% (n=4). FIG. 5B, Effects of Compound D on the displacement of [3H]-pirenzepine binding from FreeStyle 293 cell membranes expressing human M1R by ACh±Compound D. Data were expressed as percent inhibition of [$^3$H]-pirenzepine binding (n=2). FIG. 5C, Effects of Compound D on IP1 production in the hippocampus in wild-type and M1R KO mice. Compound D was administered 3 hr prior to sacrifice. Values are means+S.E.M. (n=10). Level of IP1 production was calculated as the ratio of the concentration of IP1 to that of protein in a hippocampus sample, and then it was represented as % of vehicle-treated control group. **:P≤0.01 compared with vehicle-treated group of wild-type mice by Aspin-Welch test. $^{NS}$:P>0.05 compared with vehicle-treated group of M1R KO mice by Student's t-test.

FIG. 6A-6D depicts Compound C selectively activates M1R with high α-value of 1786 in vitro and in vivo (Example 24). FIG. 6A, Structure of Compound C. FIG. 6B, Effects of Compound C on $Ca^{2+}$ response in CHO-K1 cells expressing human M1-5R. The data is expressed as a percentage when the response activity to 10 uM ACh is 100% (n=3). FIG. 6C, Effects of Compound C on the displacement of [$^3$H]-pirenzepine binding from FreeStyle 293 cell membranes expressing human M1R by ACh±Compound C. Data were expressed as percent inhibition of [$^3$H]-pirenzepine binding (n=2). FIG. 6D, Effects of Compound C on IP1 production in the hippocampus of wild-type and M1R KO mice. Compound C was administered 3 h prior to sacrifice in in vivo IP1 assay. The value is the mean+S.E.M. (n=10). Level of in vivo IP1 production was calculated as the ratio of the concentration of IP1 to that of protein in a hippocampus sample, and then it was represented as % of vehicle-treated control group (n=10). **:P≤0.01 compared with vehicle-treated group of wild-type mice by Aspin-Welch test. $^{NS}$:P>0.05 compared with vehicle-treated group of M1R KO mice by Student's t-test.

FIG. 7 depicts compared to Compound C, a MIPAM with a high α-value, Compound D has lower impact on spontaneous ileum motility in the Magnus method (Example 25). Effects of Compound C and Compound D on spontaneous ileum motility. The data is expressed as representative trace (upper figure) and mean shrinkage (%) when before treatment is 100%+S.E.M (bottom figure, n=8).

FIG. 8A-8D depicts similar to donepezil, both Compound D and Compound C improve scopolamine-induced cognitive deficits in rats in NORT (Example 26). FIG. 8A, Effects of donepezil on scopolamine-induced memory deficits. FIG. 8B, Effects of low dose of Compound D (0.03-0.3 mg/kg p.o.) on scopolamine-induced memory deficits. FIG. 8C, Effects of high dose of Compound D (0.3-3 mg/kg p.o.) on scopolamine-induced memory deficits. FIG. 8D, Effects of Compound C (0.03-3 mg/kg, p.o.) on scopolamine-induced memory deficits. Donepezil, Compound D and Compound C were orally administered 0.5, 2, and 2 h prior to the acquisition trial, respectively. Scopolamine at 0.1 mg/kg was subcutaneously administered 30 min prior to the acquisition trial. NDI was calculated using the following equation: novel object interaction time/total interaction time×100(%). Data were presented as the mean+S.E.M. (n=8). Significant difference from control group was indicated by ***P≤0.001 (Student's t-test). Significant difference from scopolamine-treated group was indicated by #P≤0.05 (two-tailed Williams' test).

FIG. 9A-9C depicts effects of donepezil, Compound D and Compound C on diarrhea induction in rats (Example 27). FIG. 9A, Effects of donepezil on diarrhea in rats. FIG. 9B, Effects of Compound D on diarrhea in rats. FIG. 9C, Effects of Compound C on diarrhea in rats. After treatment with donepezil, Compound D, and Compound C, animals were observed for 240 min (A-C). The severity of diarrhea was scored as follows: 0, normal pellets; 1, wet but formed feces; 2, swollen or mucous feces; 3, severe watery diarrhea. The maximum score during the observation was adopted. Data were presented as the mean+S.E.M. (n=6-10). #:P≤0.05 compared with vehicle-treated group by two-tailed Williams' test.

FIG. 10A-10B depicts the effects of combination of Compound D and donepezil in rats (Example 28). FIG. 10A, Effects of combination of Compound D (3 mg/kg p.o.) and donepezil (3 mg/kg p.o.) on IP1 production in rat hippocampus. Compound D and donepezil were administered 3 and 1.5 hr prior to sacrifice, respectively. Level of in vivo IP1 production was calculated as the ratio of the concentration of IP1 to that of protein in a hippocampus sample, and then it was represented as % of vehicle-treated control group. Values are means+S.E.M. of 6 rats per group. :P≤0.01 compared with vehicle+vehicle-treated (control) group by Dunnett's multiple comparison test. FIG. 10B, Combination of sub-effective doses of Compound D and donepezil improve scopolamine-induced cognitive deficits in NORT in rats. Compound D (0.1 mg/kg p.o.) and donepezil (0.1 mg/kg p.o.) were administered 2 and 0.5 h prior to the acquisition trial, respectively. Scopolamine at 0.1 mg/kg was subcutaneously administered 30 min prior to the acquisition trial. NDI was calculated using the following equation: novel object interaction time/total interaction time×100(%). Data were presented as the mean+S.E.M. (n=8). :P≤0.01 compared with vehicle (p.o.)+vehicle (s.c.)-treated control group by Student's t-test. #:P≤0.05 compared with vehicle (p.o.)+scopolamine (s.c.)-treated group by Dunnett's multiple comparison test.

FIG. 11A, Time course of plasma concentration of donepezil. FIG. 11B, Time course of plasma concentration of Compound D. Compound D 0.1 mg/kg, p.o. or dosing vehicle was administered at 0 h (1st dose). 1.5 h after 1st dosing, donepezil 0.1 mg/kg, as a free form (HCl salt), p.o. was administered. Values are mean+SD of 5 rats per group.

FIG. 12 depicts combination of Compound C and donepezil at sub-effective doses did not improve scopolamine-induced cognitive deficits in NORT in rats (Example 29). Compound C (0.03 mg/kg) and donepezil (0.1 mg/kg) were orally administered at 2 and 0.5 hr prior to the acquisition trial, respectively. Scopolamine at 0.1 mg/kg was s.c. administered 0.5 hr prior to the acquisition trial. NDI was calculated using the following equation: novel object interaction time/total interaction time×100(%). The data shows the mean+S.E.M. (n=8). ***:P≤0.001 compared with vehicle (p.o.)+vehicle (s.c.) control group by Student's t-test.

FIG. 13 depicts contrary to carbachol and Compound C, Compound D revealed only ADP generation (Example 30). (A) Chart recording of the membrane potential of layer 5 pyramidal neuron with bath-applied carbachol (10 uM for 10 min). Brief current steps (~450 pA) delivered at 20 s intervals generated short periods of activity.

FIG. 13 depicts contrary to carbachol and Compound C, Compound D revealed only ADP generation (Example 30). (B) Individual responses to current injections shown at a faster timescale, with expanded views of the AHPs and ADPs.

FIG. 13 depicts contrary to carbachol and Compound C, Compound D revealed only ADP generation (Example 30). (C) Summary of effects of carbachol on AHP (left), ADP (middle), and RMP (right) amplitudes.

FIG. 13 depicts contrary to carbachol and Compound C, Compound D revealed only ADP generation (Example 30). (D) Summary graph comparing mean changes in AHPs, ADPs, and RMPs amplitudes following application of Compound D. Values are means±S.E.M. (n=5). For statistical evaluation of the results, a multiple-group comparison was performed by ANOVA followed by Dunnett's test for paired data. *P≤0.05, **P≤0.01 compared with vehicle-treated group.

FIG. 13 depicts contrary to carbachol and Compound C, Compound D revealed only ADP generation (Example 30). (E) Summary graph comparing mean changes in AHPs, ADPs, and RMPs amplitudes following application of Compound C. Values are means+S.E.M. (n=5). For statistical evaluation of the results, a multiple-group comparison was performed by ANOVA followed by Dunnett's test for paired data. *P≤0.05, **:P≤0.01 compared with vehicle-treated group.

FIG. 14 depicts combination of sub-effective doses of Compound D and rivastigmine improve scopolamine-induced cognitive deficits in NORT in rats (Example 31). Compound D (0.1 mg/kg, p.o.) and rivastigmine (0.1 mg/kg, i.p.) were administered 2 and 0.5 hr prior to the acquisition trial, respectively. Scopolamine at 0.1 mg/kg was subcutaneously administered 0.5 hr prior to the acquisition trial. NDI was calculated using the following equation: novel object interaction time/total interaction time×100(%). Data were presented as the mean+S.E.M. (n=8). **:P≤0.01 compared with vehicle (p.o.)+vehicle (s.c.) control group by Student's t-test. #:P≤0.01 compared with vehicle (p.o.)+scopolamine (s.c.)-treated group by Dunnett's multiple comparison test.

FIG. 15 shows a sequence of a nucleic acid encoding human M1R (SEQ ID NO: 1).

FIG. 16 shows the amino acid sequence of human M1R (SEQ ID NO: 2).

DESCRIPTION OF EMBODIMENTS

Detailed Description of the Invention

Figure 1:
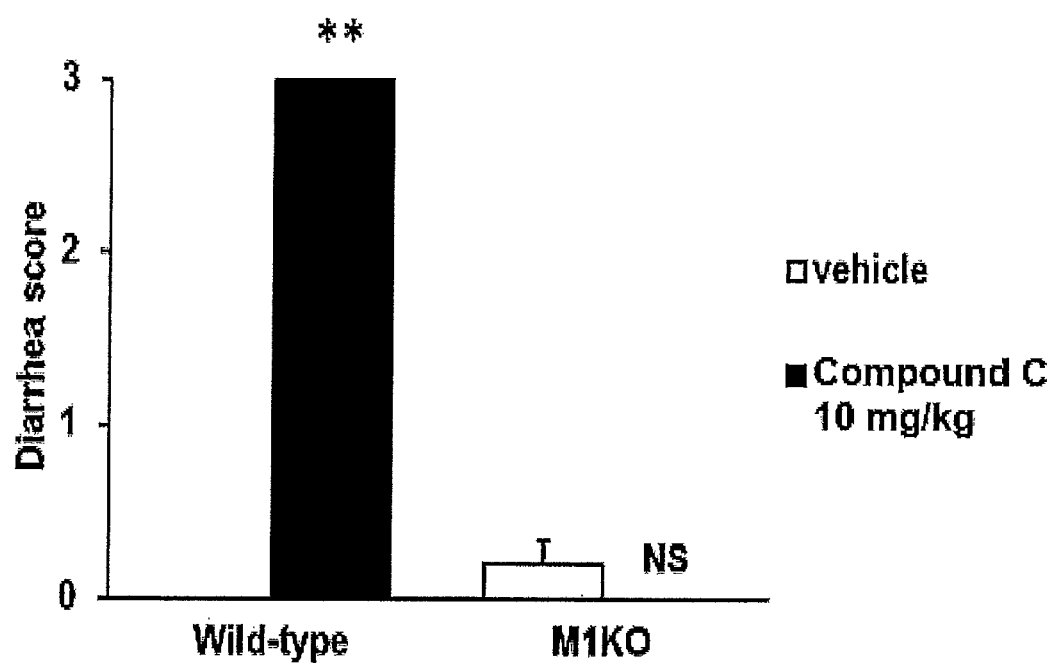
FIG. 1 depicts diarrhea induction by Compound C treatment in WT and M1R KO mice (hereinafter sometimes to be indicated as "MIKO mouse" in the present DESCRIPTION) (Example 11). Mice were observed for 120 min after treatment with Compound C. The severity of diarrhea was scored as follows: 0, normal pellets; 1, wet but formed feces; 2, swollen or mucous feces; 3, severe watery diarrhea. The maximum score during the observation was adopted. Data were presented as the mean+S.E.M. (n=10). **:$P \leq 0.01$ compared with vehicle-treated group of WT mice by Aspin-Welch test. $^{NS}$:$P > 0.05$ compared with vehicle-treated group of M1R KO mice by Student's T-test.

The present invention is explained as follows.

In the present DESCRIPTION, abbreviations for amino acid, (poly)nucleotides, and the like follow IUPAC-IUB regulations (IUPAC-IUB Communication on Biological Nomenclature, Eur. J. Biochem., 138: 9 (1984)), the "Guidelines for the creation of specifications, and the like containing base sequence or amino acid sequence" (edited by the Japan Patent Office), and conventional symbols in the relevant field.

In the present DESCRIPTION, the "cholinergic side effect" means a side effect caused by an enhanced choline stimulating action. Specific examples thereof include diarrhea, sick feeling, vomiting, salivation, sweating, bradycardia, hypotension, respiratory suppression, collapse, convulsion, nausea, promoted gastric acid secretion, sleep disorder, anorexia, fatigue, eye tearing, constricted pupil and the like. A side effect that can be reduced preferably is a cholinergic side effect caused by M1R. Diarrhea is more preferably reduced.

In the present DESCRIPTION, the "cholinergic disorder" means a disorder caused by neuronal degeneration or functional disorder in cholinergic neurotransmission, and includes a state in which at least one mechanism of action of ACh does not function normally, such as synthesis of ACh, storage in endoplasmic reticulum, secretion, binding to or degradation of receptor (muscarinic or nicotinic) and the like. Specific examples of the disease relating to the "cholinergic disorder" include Alzheimer's disease, schizophrenia, Parkinson's disease with dementia or dementia with Lewy bodies and the like.

In the present DESCRIPTION, the "decreased cholinergic side effect" means that M1PAM has wider safety margin between the minimal cognition effective dose and the minimal cholinergic side effect dose in mammals (e.g., mouse, rat, hamster, rabbit, cat, dog, bovine, sheep, monkey, human). The margin of safety is calculated from minimal cholinergic side effect dose/minimal cognition effective dose. The margin of safety is preferably not less than 2-fold, more preferably not less than 5-fold, further preferably not less than 10-fold, further preferably not less than 20-fold, particularly preferably not less than 30-fold. In another embodiment, the margin of safety is preferably 2- to 10,000-fold, more preferably 5- to 1,000-fold. Further preferably, it is 10- to 500-fold, further more preferably 20- to 250-fold. Particularly preferably, it is 30- to 100-fold. The mammal is preferably mouse. In another embodiment, the mammal is preferably rat. In yet another embodiment, the mammal is preferably human.

In the present DESCRIPTION, the "α value" is a value showing the binding cooperativity between M1PAM and acetylcholine (sometimes to be abbreviated as "ACh" in the present DESCRIPTION) (Wootten, D. et. al., Nat Rev Drug Discov. 2013 August; 12(8):630-44).

In the present invention, the "α value" can be calculated from, for example, the allosteric ternary complex model described in the below-mentioned numerical formulas (i)-(iii).

In the present DESCRIPTION, M1PAM may be in any form such as protein, peptide, antibody, nonpeptidic compound and the like. M1PAM is preferably a nonpeptidic compound.

(1) Screening for M1PAM with Reduced Cholinergic Side Effects Using α Value as Index The present invention provides a method for screening for M1PAM with reduced cholinergic side effects by using α value as an index.

As regards α value to be the index in the screening method of the present invention, M1PAM with a low α value is expected to reduce cholinergic side effects. In addition, M1PAM with a low α value may show a superior effect of combined use with an acetylcholinesterase inhibitor (e.g., donepezil, rivastigmine, galanthamine) for the prophylaxis or treatment of Alzheimer's disease, schizophrenia, Parkinson's disease with dementia, dementia with Lewy bodies and the like. Thus, M1PAM with a low α value can be used as a prophylactic or therapeutic drug for Alzheimer's disease, schizophrenia (positive symptom selected from the group consisting of dillusions, delusion, delusive disorder, paranoia, disorganized conversations, disruption of logical thought process (e.g., distracted, disordered, illogical or odd), and combinations thereof; negative symptom selected from the group consisting of withdrawal, apathy, flattening of emotion, anhedonia, lack of social interaction, reduced motivation, rigidity or firmness of thought, flat emotion or dullness of emotion, decrease in concrete thoughts, failure of motivation, poor spontaneity, poor initiative and combinations thereof; cognitive symptom selected from the group consisting of lack of attention, lack of ability to name objects, lack of working memory, lack of accumulation of long-term memory, lack of ability to execute, delay in information processing, delay in neural activity, long-term depression, and combinations thereof), Parkinson's disease with dementia or dementia with Lewy bodies and the like, where the drug is expected to reduce a cholinergic side effects and/or show a superior effect of combined use with an acetylcholinesterase inhibitor (e.g., donepezil, rivastigmine, galanthamine).

Therefore, the α value can be used as an index for screening for M1PAM with reduced cholinergic side effects and/or M1PAM expected to show a superior combined use effect with an acetylcholinesterase inhibitor (e.g., donepezil, rivastigmine, galanthamine) in the prophylaxis or treatment of Alzheimer's disease, schizophrenia, Parkinson's disease with dementia, dementia with Lewy bodies and the like.

A method for screening for M1PAM with reduced cholinergic side effects by using α value as an index includes (A) a method characteristically using detectable ACh, (B) a method characteristically using detectable cholinergic muscarinic M1 receptor antagonist (M1 antagonist), (C) a method characteristically using detectable M1PAM and the like, which are described in detail below.

(A) Screening Method Characteristically Using Detectable Ach

This screening method includes the following steps:
(a) contacting M1R or a partial peptide thereof with a test compound and detectable ACh,
(b) measuring α value of the test compound, and
(c) selecting M1PAM with a low α value.

In the screening method (A), the α value can be calculated from the following allosteric ternary complex model (numerical formula (i)) (Price, M. R. et. al., Mol. Pharmacol. 2005 November; 68(5): 1484-95).

[numerical formula 1]

$$Y = \frac{\frac{[A]}{K_A} + \frac{\alpha[A][B]}{K_A K_B}}{1 + \frac{[A]}{K_A} + \frac{[B]}{K_B} + \frac{\alpha[A][B]}{K_A K_B}} \quad (i)$$

where Y is the percentage of specific binding; [A] and [B] are respectively the concentration of detectable ACh and the test compound; $K_A$ and $K_B$ are respectively the equilibrium dissociation constant of detectable ACh and the test compound; and a is the cooperativities between the test compound and detectable ACh. Values of cooperativity greater than 1 show positive cooperativity (allosteric enhancement of orthosteric ligand binding) and values of cooperativity less than 1 show negative cooperativity (allosteric inhibition of orthosteric ligand binding).

(B) Screening Method Characteristically Using Detectable M1 Antagonist

This screening method includes the following steps:
(a) contacting M1R or a partial peptide thereof with a test compound, ACh and detectable M1 antagonist,
(b) measuring α value of the test compound, and
(c) selecting M1PAM with a low α value.

In the screening method (B), the α value can be calculated as $\alpha_{AB}$ from the following allosteric ternary complex model (numerical formula (ii)) (Davie, B. J. et. al., J. Med. Chem. 2014 Jun. 26; 57(12):5405-18).

[numerical formula 2]

$$Y = \frac{\frac{[C]}{K_C} + \frac{\alpha_{BC}[B][C]}{K_B K_C}}{1 + \frac{[A]}{K_A} + \frac{[B]}{K_B} + \frac{[C]}{K_C} + \frac{\alpha_{AB}[A][B]}{K_A K_B} + \frac{\alpha_{BC}[B][C]}{K_B K_C}} \quad (ii)$$

wherein Y is the percentage of specific binding; [A], [B], and [C] are respectively the concentration of ACh, the test compound and detectable M1 antagonist; $K_A$, $K_B$ and $K_C$ respectively show the equilibrium dissociation constant of ACh, the test compound and detectable M1 antagonist; and $\alpha_{AB}$ and $\alpha_{BC}$ are respectively the cooperativities between the test compound and ACh, and the test compound and detectable M1 antagonist. Values of cooperativity greater than 1 show positive cooperativity (allosteric enhancement of orthosteric ligand binding) and values of cooperativity less than 1 show negative cooperativity (allosteric inhibition of orthosteric ligand binding).

The M1 antagonist used in the screening method (B) is not particularly limited. For example, pirenzepine, quinuclidinyl benzilate (QNB), N-methyl scopolamine, telenzepine, atropine, 4-diphenylacetoxy-N-methylpiperidine methiodide (4-DAMP), 8-[4-[3-[4-[3-[[4-(1-aza bicyclo[2.2.2]octan-8-yl)-1,2,5-thiadiazol-3-yl]oxy]prop-1-ynyl]phenyl]prop-2-ynoxy]-1,2,5-thiadiazol-3-yl]-1-aza bicyclo[2.2.2]octane, 8-[4-[3-[3-[3-[[4-(1-aza bicyclo[2.2.2]octan-8-yl)-1,2,5-thiadiazol-3-yl]oxy]prop-1-ynyl]phenyl]prop-2-ynoxy]-1,2, 5-thiadiazol-3-yl]-1-aza bicyclo[2.2.2]octane, pentylthio-TZTP, 8-[4-(3-phenylprop-2-ynoxy)-1,2,5-thiadiazol-3-yl]-1-aza bicyclo[2.2.2]octane, xanomeline, sabcomeline, arecaidine propargylester, N-[(1R,2R)-6-[1-[(4-fluorophenyl)methyl-methylamino]ethylideneamino]-2-hydroxy-2,3-dihydro-1H-inden-1-yl]-4-phenylbenzamido, 4-(4-butylpiperidin-1-yl)-1-(2-methylphenyl)butan-1-one, oxotremorine, arecoline, oxotremorine-M, oxotremorine, 4-[(3-chlorophenyl)carbamoyloxy]but-2-ynyl-trimethylazanium chloride, pilocarpine, milameline, methyl furmethide, (2R)-2,8-dimethyl-3-methylidene-1-oxa-8-azaspiro[4.5]decane, 2,8-dimethyl-3-methylidene-1-oxa-8-azaspiro[4.5]decane, carbachol, furtrimethonium, bethanechol, propan-2-yl 4-[4-[(3aS,7aS)-2-oxo-3a,4,5,6,7,7a-hexahydro-3H-benzimidazol-1-yl]piperidin-1-yl]-4-methylpiperidine-1-carboxylate, metacholine, (3S)-3-(acetyloxy)-1-aza bicyclo[2.2.2]octan-1-ium, [(8R)-1-azonia bicyclo[2.2.2]octan-8-yl]acetate, butylthio-TZTP and the like can be mentioned. Preferred are pirenzepine, QNB, N-methyl scopolamine, telenzepine, atropine and 4-DAMP. More preferred is pirenzepine. These M1 antagonists may be novel or known.

(C) Screening Method Characteristically Using Detectable M1PAM

This screening method includes the following steps:
(a) contacting M1R or a partial peptide thereof with a test compound, detectable M1PAM and ACh,
(b) measuring α value of the test compound, and
(c) selecting M1PAM with a low α value.

In the screening method (C), the α value can be calculated as $\alpha_{AB}$ from the following allosteric ternary complex model (numerical formula (iii)).

[numerical formula 3]

$$Y = \frac{\frac{[C]}{K_C} + \frac{\alpha_{AC}[A][C]}{K_A K_C}}{1 + \frac{[A]}{K_A} + \frac{[B]}{K_B} + \frac{[C]}{K_C} + \frac{\alpha_{AB}[A][B]}{K_A K_B} + \frac{\alpha_{AC}[A][C]}{K_A K_C}} \quad \text{(iii)}$$

wherein Y is the percentage of specific binding; [A], [B], and [C] are respectively the concentration of ACh, the test compound and detectable M1PAM; $K_A$, $K_B$ and $K_C$ respectively show the equilibrium dissociation constant of ACh, the test compound and detectable M1PAM; and $\alpha_{AB}$ and $\alpha_{AC}$ are respectively the cooperativities between ACh and the test compound, and ACh and detectable M1PAM. Values of cooperativity greater than 1 show positive cooperativity (allosteric enhancement of orthosteric ligand binding) and values of cooperativity less than 1 show negative cooperativity (allosteric inhibition of orthosteric ligand binding).

While the detectable M1PAM used in the screening method (C) is not particularly limited, it may be, for example, M1PAM described in WO 2013/129622, WO 2014/077401, WO 2015/174534, WO 2015/163485, WO 2015/190564, WO 2016/208775, WO 2017/069173 or PCT/JP2017/009529; benzyl quinolone carboxylic acid (BQCA) or the like. These M1PAMs may be novel or known.

In the above-mentioned screening methods (A)-(C), M1R or a partial peptide thereof may be an isolated M1R or a partial peptide thereof, or may be expressed in a cell capable of producing M1R or a partial peptide thereof.

As M1R, a protein containing an amino acid sequence the same or substantially the same as the amino acid sequence shown by SEQ ID NO:2 can be mentioned. M1R may be a protein derived from a cell or tissue of a mammal (preferably human), or a synthesized protein.

Examples of the amino acid sequence substantially the same as the amino acid sequence shown by SEQ ID NO:2 include an amino acid sequence having about 80% or more, preferably about 90% or more, more preferably about 95% or more, identity with the amino acid sequence shown by SEQ ID NO:2, and the like.

As the protein containing an amino acid sequence substantially the same as the amino acid sequence shown by SEQ ID NO:2 in the present invention, for example, a protein having an amino acid sequence substantially the same as the amino acid sequence shown by SEQ ID NO:2 and activity (e.g., ligand binding activity, signal transduction activity) substantially equivalent to that of a protein consisting of the amino acid sequence shown by SEQ ID NO: 2 is preferable.

M1R is preferably a human-derived 141R consisting of the amino acid sequence shown by SEQ ID NO: 2.

As the partial peptide of M1R, for example, a peptide having an amino acid sequence partially same as that of the above-mentioned M1R and substantially the same activity (e.g., ligand binding activity, signal transduction activity) is used. The number of amino acids constituting the partial peptide is at least 20, preferably not less than 50, more preferably not less than 100, of the amino acid sequence constituting M1R.

In the above-mentioned screening methods (A)-(C), M1R or a partial peptide thereof may be isolated and purified from a cell or tissue producing the M1R or the partial peptide thereof, or chemically synthesized or produced as a recombinant protein by genetic engineering.

The M1R or a partial peptide thereof can be contacted with a test compound and the like in, for example, water or a suitable buffer. The concentration of the test compound in water or buffer varies depending on the kind of the test compound (solubility, toxicity etc.). It is appropriately selected within the range of, for example, about 0.1 nM-about 30,000 nM. Incubation may be performed during the contact. The incubation time is, for example, about 10 min-about 24 hr.

The cell capable of producing the above-mentioned M1R or a partial peptide thereof is not particularly limited as long as it is a human or other mammalian cell that inherently expresses same or a biological sample containing the cell (e.g., blood, tissue, organ). Suspension cell lines (including adherent cells obtained by culturing by stirring culture, shaking culture, gyratory culture (e.g., gyratory shaking culture), micro carrier culture or culture in serum-free medium and the like and cultured in suspension) (e.g., floating HEK293 cell line) are preferable. When blood, tissue, organ and the like derived from a non-human animal are used, they may be isolated from the living organism and cultured, or M1PAM may be administered to the living organism itself, and a biological sample may be isolated after lapse of a given time.

Examples of the cell capable of producing M1R or a partial peptide thereof include various transformants produced by a conventionally known genetic engineering technique. Examples of the host to be used for the technique include mammalian cell, for example, HepG2 cell, HEK293 cell (floating HEK293 cell (e.g., including FreeStyle 293 cell), H4IIE-C3 cell, HeLa cell, LNCaP-FGC cell, PC-3 cell, DU-145 cell, human FL cell, monkeyCOS-7 cell, monkey Vero cell, Chinese hamster ovary cell (hereinafter sometimes to be abbreviated as CHO cell) (floating CHO cell (e.g., including FreeStyle CHO cell)), dhfr gene defective CHO cell (hereinafter sometimes to be abbreviated as CHO (dhfr$^-$) cell), mouse L cell, mouse AtT-20 cell, mouse myeloma cell, rat H4IIE-C3 cell, rat GH3 cell and the like. In addition, cells that do not inherently express M1R can also be used as a host.

Specifically, the transformant can be prepared by linking a DNA encoding M1R (i.e., DNA encoding a protein containing the amino acid sequence shown by SEQ ID NO: 2) to the downstream of a promoter in a suitable expression vector and introducing the vector into a host animal cell.

DNA encoding M1R can be cloned, for example, by synthesizing a suitable oligonucleotide as a probe or primer based on the nucleotide sequence shown by SEQ ID NO: 1, and by using a hybridization method or PCR method, from a cDNA or cDNA library derived from a cell or tissue that produces the aforementioned M1R. The hybridization can be performed, for example, by the method described in Molecular Cloning, 2nd ed. (J. Sambrook et al., Cold Spring Harbor Lab. Press, 1989) and the like. When a commercially available library is used, the hybridization can be performed according to the instructions attached to the library.

The nucleotide sequence of the DNA can be converted according to a method known per se, such as the ODA-LA PCR method, the Gapped duplex method, or the Kunkel method, or a method based thereon, using a commonly known kit, for example, Mutan™-super Express Km (TAKARA SHUZO CO. LTD.), Mutan™-K (TAKARA SHUZO CO. LTD.) and the like. For example, a part or the entirety of the region that does not cause disappearance of the function of M1R even if deleted, such as TAUS region and the like, may be deleted from a cloned DNA or the entirety or a part of the deleted region may be inserted into or added to a DNA encoding M1R lacking a part of the region.

The cloned DNA can be used as is, or after digestion with a restriction endonuclease or addition of a linker as desired, depending on the purpose of its use. The DNA may have the translation initiation codon ATG at the 5' end thereof, and the translation stop codon TAA, TGA or TAG at the 3' end thereof. These translation initiation codons and translation stop codons can be added by using a suitable synthetic DNA adaptor.

As an expression vector, animal cell expression plasmid (e.g., pA1-11, pXT1, pRc/CMV, pRc/RSV, pcDNAI/Neo); bacteriophage such as Aphage and the like; animal virus vectors such as retrovirus, vaccinia virus, adenovirus, lentivirus and the like; and the like are used. The promoter may be any promoter, as long as it is appropriate for the host used to express the gene. For example, SRa promoter, SV40 promoter, LTR promoter, CMV (cytomegalovirus) promoter, RSV (Rous sarcoma virus) promoter, MoMuLV (Moloney murine leukaemia virus) LTR, HSV-TK (herpes simplex virus thymidine kinase) promoter and the like are used. Of these, CMV promoter, SRα promoter and the like are preferred.

Useful expression vectors include, in addition to the above, expression vectors that optionally comprises an enhancer, a splicing signal, a polyA addition signal, a selection marker, an SV40 replication origin (hereinafter also abbreviated as SV40 ori), and the like. As examples of the selection markers, the dihydrofolate reductase gene (hereinafter also abbreviated as dhfr) [methotrexate (MTX) resistance], the ampicillin resistance gene (hereinafter also abbreviated as amp$^r$), the neomycin resistance gene (hereinafter also abbreviated as neo$^r$, G418 resistance), and the like can be mentioned. In particular, when a dhfr gene defective Chinese hamster cell is used and the dhfr gene is used as the selection marker, a target gene can also be selected using a thymidine-free medium.

A cholinergic muscarinic M1 receptor or partial peptide expressing cell can be produced by transforming a host with an expression vector containing the above-mentioned DNA encoding M1R or a partial peptide.

Transformation can be performed by a calcium phosphate coprecipitation method, a PEG method, an electroporation method, a microinjection method, a lipofection method and the like. For example, the method described in *Saibo Kogaku*, extra issue 8, *Shin Saibo Kogaku Jikken Protocol*, 263-267 (1995), published by Shujunsha, or *Virology*, 52, 456 (1973) can be used.

The transformed cell obtained as mentioned above, a mammalian cell inherently having an ability to produce cholinergic muscarinic M1 receptor or a partial peptide thereof, and a tissue or organ containing the cell can be cultivated in a medium, for example, minimum essential medium (MEM) containing about 5-20% fetal bovine serum [Science, vol. 122, 501(1952)], Dulbecco's modified Eagle medium (DMEM) [Virology, vol. 8, 396(1959)], RPMI1640 medium [The Journal of the American Medical Association, vol. 199, 519(1967)], 199 medium [Proceeding of the Society for the Biological Medicine, vol. 73, 1(1950)] and the like. The medium preferably has a pH of about 6-8. Culture is performed generally at about 30-40° C., and aeration and stirring may be performed as necessary.

In the above-mentioned screening method, M1R or a partial peptide thereof can also be contacted with a test compound and the like by, for example, culturing a cell capable of producing M1R in the presence of a test compound and the like.

The test compound to be used in the above-mentioned screening methods (A)-(C) is not particularly limited as long as it has M1PAM activity. Examples of the test compound include substances such as protein, peptide, antibody, non-peptidic compound, fermentation product, cell extract, plant extract, animal tissue extract, plasma and the like, which may be novel or known. Specific examples of the test compound include M1PAMs described in WO 2013/129622, WO 2014/077401, WO 2015/174534, WO 2015/163485, WO 2015/190564, WO 2016/208775 or PCT/JP2017/009529 and the like can be mentioned.

A test compound can be contacted with the above-mentioned M1R or partial peptide or cells producing these by, for example, adding the test compound to the above-mentioned medium and various buffers (e.g., HEPES buffer, phosphate buffer, phosphate buffered saline, Tris-HCl buffer, borate buffer, acetate buffer and the like), and incubating the cell for a given time. While the concentration of the test compound to be added varies depending on the kind of the compound (solubility, toxicity etc.), it is, for example, appropriately determined within the range of about 0.1 nM-about 10000 nM, preferably about 1 nM-about 1000 nM. Examples of the incubation time include about 10 min-about 24 hr.

When M1R or partial peptide-producing cell is provided in the form of a non-human mammal individual, the condition of the individual animal is not particularly limited. For example, a transgenic non-human mammal into which a nucleic acid containing a protein coding sequence (CDS) of M1R or a partial peptide in an expressible form is introduced can be used. Such transgenic animal can be produced by a conventional method.

While the rearing conditions of the animal to be used are not particularly limited, the animal is preferably reared in an environment of SPF grade or above. A test compound is contacted with the cell by the administration of the test compound to the individual. While the administration route is not particularly limited, for example, intravenous administration; intraarterial administration, subcutaneous administration, intradermal administration, intraperitoneal administration, oral administration, tracheobronchial administration, rectal administration and the like can be mentioned. While the dose is not particularly limited, either, for example, a dose of about 0.5-20 mg/kg can be administered 1-5 times, preferably 1-3 times, per day for 1-14 days.

In the above-mentioned screening methods (A)-(C), a method for measuring detectable ACh, detectable cholinergic muscarinic M1 receptor agonist or detectable M1PAM (hereinafter sometimes to be abbreviated as detectable substance) includes a measurement method using a labeling substance and a measurement method not using a labeling substance.

In the present invention, "detectable" means that the binding between a detectable substance and M1R or a partial peptide thereof can be detected using a measurement method using a labeling substance, a measurement method not using a labeling substance, or the like.

As examples of the measurement method using a labeling agent, a method using a radioisotope, an enzyme, a fluorescent substance, a luminescent substance or the like as the labeling substance can be mentioned. As the radioisotope, [$^{125}$I], [$^{131}$I], [$^{3}$H], [$^{14}$C] and the like can be used. As the above-described enzyme, those that are stable and high in specific activity are preferred; for example, β-galactosidase, β-glucosidase, alkaline phosphatase, peroxidase, malate dehydrogenase and the like can be used. As examples of the fluorescent substance, fluorescamine, fluorescein isothiocyanate, and the like can be used. As examples of the luminescent substance, luminol, luminol derivative, luciferin, lucigenin and the like can be used. Furthermore, a biotin-(strepto)avidin system can also be used for binding of an antibody or an antigen and a labeling agent. Preferably, a radioisotope is used.

As examples of the measurement method not using a labeling agent, surface plasmon resonance (SPR) method (Chu, R. et. al., Sci. Rep. 2014 Dec. 8; 4:7360), ASMS METHOD (Whitehurst, C. E. et al., J. Biomol. Screen. 2006 March; 11(2):194-207), Back-Scattering Interferometry (BSI) method (Molecular Sensing, Baksh, M. M. et al., Nat Biotechnol. 2011 April; 29(4):357-60), Nuclear Magnetic Resonance (NMR) method and Isothermal Titration calorimetry (ITC) method can be mentioned.

For example, in the above-mentioned screening methods (A)-(C), when the α value of the test compound calculated from each of the numerical formulas (i)-(iii) is greater than about 0 and not more than about 1,000, preferably greater than about 0 and not more than about 800, more preferably greater than about 0 and not more than about 500, the test compound can be selected as M1PAM with a low α value. In another embodiment, when the α value of the test compound is greater than about 1 and not more than about 1,000, preferably greater than about 1 and not more than about 800, more preferably greater than about 1 and not more than about 500, the test compound can be selected as M1PAM with a low α value. In yet another embodiment, when the α value of the test compound is not less than about 10 and not more than about 1,000, preferably not less than about 10 and not more than about 800, more preferably not less than about 10 and not more than about 500, the test compound can be selected as M1PAM with a low α value. The thus-selected M1PAM with low α value is M1PAM with reduced cholinergic side effects.

(2) Treatment Method Using M1PAM with Low α Value

In the treatment method of the present invention, the low α value is an α value greater than about 0 and not more than about 1,000, preferably greater than about 0 and not more than about 800, more preferably greater than about 0 and not more than about 500. In another embodiment, the low α value is an α value greater than about 1 and not more than about 1,000, preferably greater than about 1 and not more than about 800, more preferably greater than about 1 and not more than about 500. In yet another embodiment, the low α value is an α value not less than about 10 and not more than about 1,000, preferably not less than about 10 and not more than about 800, more preferably not less than about 10 and not more than about 500. These α values are measured by the method described in the binding assay of Example 4 and data analysis of Example 9, or a method analogous thereto.

Examples of the "M1PAM with a low α value (sometimes to be abbreviated as "the compound of the present invention)" in the present DESCRIPTION)" used in the treatment method of the present invention include the compounds described in WO 2013/129622, WO 2014/077401, WO 2015/174534, WO 2015/163485, WO 2015/190564, WO 2016/208775, PCT/JP2017/009529 and the like. The M1PAM with a low α value selected by the above-mentioned screening methods (A)-(C) is also included in the compound of the present invention. The compound of the present invention is preferably a compound such as 1,5-anhydro-2,3-dideoxy-3-({[5,8-difluoro-1-(4-methoxybenzyl)-4-oxo-1,4-dihydroquinolin-3-yl]carbonyl}amino)-DL-threo-pentitol, 5,8-difluoro-N-[(1,2-trans)-2-hydroxycyclohexyl]-1-(4-methoxybenzyl)-4-oxo-1,4-dihydroquinoline-3-carboxamide, 8-fluoro-N-[(1,2-trans)-2-hydroxycyclopentyl]-4-oxo-1-[4-(1H-pyrazol-1-yl)benzyl]-1,4-dihydroquinoline-3-carboxamide, 1-[4-(1,3-dimethyl-1H-pyrazol-4-yl)benzyl]-N-[(1,2-trans)-2-hydroxycyclopentyl]-4-oxo-1,4-dihydroquinoline-3-carboxamide, 2-(4-(1-methyl-1H-pyrazol-4-yl)benzyl)-7-((tetrahydrofuran-2-yl)methoxy)isoindolin-1-one, 3-fluoro-2-((2-(4-(1-methyl-1H-pyrazol-4-yl)benzyl)-3-oxo-2,3-dihydro-1H-isoindol-4-yl)oxy)benzonitrile, 4-((2,4-difluorobenzyl)oxy)-6-(4-(1-methyl-1H-1,2,3-triazol-4-yl)benzyl)-6,7-dihydro-5H-pyrrolo[3,4-d]pyrimidin-5-one, 4-((4-(2-fluoro-4-(trifluoromethyl)phenoxy)-3-oxo-1,3-dihydro-2H-pyrrolo[3,4-c]pyridin-2-yl)methyl)benzamide, difluoroethoxy)-2-(4-(1,3-dimethyl-1H-pyrazol-4-yl)benzyl)-1,2-dihydro-3H-pyrrolo[3,4-c]pyridin-3-one, 4-(2,2-difluoropropoxy)-6-(4-(1,3-dimethyl-1H-pyrazol-4-yl)benzyl)-6,7-dihydro-5H-pyrrolo[3,4-d]pyrimidin-5-one, 4-(2,2-difluoropropoxy)-6-(4-(1,3-dimethyl-1H-pyrazol-4-yl)-2-fluorobenzyl)-6,7-dihydro-5H-pyrrolo[3,4-d]pyrimidin-5-one, 2-[(3S,4S)-4-hydroxytetrahydro-2H-pyran-3-yl]-6-(4-methoxybenzyl)-4,5-dimethyl-2,3-dihydro-1H-isoindol-1-one, 4-fluoro-2-[(3S,4S)-4-hydroxytetrahydro-2H-pyran-3-yl]-5-methyl-6-[4-(1H-pyrazol-1-yl)benzyl]-2,3-dihydro-1H-isoindol-1-one, 2-((1S,2S)-2-hydroxycyclohexyl)-4,5-dimethyl-6-((6-methylpyridin-3-yl)methyl)isoindolin-1-one, 8-fluoro-3-((1S,2S)-2-hydroxycyclopentyl)-7-methyl-6-((6-(1H-pyrazol-1-yl)pyridin-3-yl)methyl)-2,3-dihydro-4H-1,3-benzoxazin-4-one, 8-chloro-6-((6-chloropyridin-3-yl)methyl)-3-((1S,2S)-2-hydroxycyclopentyl)-7-methyl-2,3-dihydro-4H-1,3-benzoxazin-4-one, 3-(trans-2-hydroxycyclohexyl)-7-methyl-6-((6-methylpyridin-3-yl)methyl)-2,3-dihydro-4H-1,3-benzoxazin-4-one, 3-((3S,4S)-4-hydroxytetrahydro-2H-pyran-3-yl)-7-methyl-6-(4-(1-methyl-1H-pyrazol-3-yl)benzyl)-2,3-dihydro-4H-1,3-benzoxazin-4-one, N-((1S,2S)-2-hydroxycyclopentyl)-5-methyl-4-(4-(1-methyl-1H-pyrazol-3-yl)benzyl)pyridine-2-carboxamide, N-((1S,2S)-2-hydroxycyclopentyl)-5,6-dimethyl-4-(4-(1-methyl-1H-pyrazol-3-yl)benzyl)pyridine-2-carboxamide, N-((1S,2S)-2-hydroxycyclohexyl)-5,6-dimethyl-4-((6-(1-methyl-1H-pyrazol-3-yl)pyridin-3-yl)methyl)pyridine-2-carboxamide or the like or a salt thereof.

Examples of such salt include salts with inorganic base, a salt with organic base, a salt with inorganic acid, a salt with organic acid, a salt with basic or acidic amino acid.

Preferable examples of salts with inorganic base include alkali metal salt such as sodium salt, potassium salt and the like; alkaline earth metal salt such as calcium salt, magnesium salt and the like; and aluminum salt and ammonium salt.

Preferable examples of salts with organic base include salts with trimethylamine, triethylamine, pyridine, picoline, ethanolamine, diethanolamine, triethanolamine, tromethamine[tris(hydroxymethyl)methylamine], tert-butylamine, cyclohexylamine, benzylamine, dicyclohexylamine and N,N-dibenzylethylenediamine.

Preferable examples of salts with inorganic acid include salts with hydrogen chloride, hydrogen bromide, nitric acid, sulfuric acid and phosphoric acid.

Preferable examples of salts with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid and p-toluenesulfonic acid.

Preferable examples of salts with basic amino acid include salts with arginine, lysine and ornithine.

Preferable examples of salts with acidic amino acid include salts with aspartic acid and glutamic acid.

Among these salts, a pharmaceutically acceptable salt is preferable.

The compound of the present invention is effective as a prophylactic or therapeutic drug for, for example, Alzheimer's disease, schizophrenia (positive symptom selected from dillusions, delusion, delusive disorder, paranoia, disorganized conversations, disruption of logical thought process (e.g., distracted, disordered, illogical or odd), and combinations thereof; negative symptom selected from the group consisting of withdrawal, apathy, flattening of emotion, anhedonia, lack of social interaction, reduced motivation, rigidity or firmness of thought, flat emotion or dullness of emotion, decrease in concrete thoughts, failure of motivation, poor spontaneity, poor initiative and combinations thereof; cognitive symptom selected from the group consisting of lack of attention, lack of ability to name objects, lack of working memory, lack of accumulation of long-term memory, lack of ability to execute, delay in information processing, delay in neural activity, long-term depression, and combinations thereof), Parkinson's disease with dementia or dementia with Lewy bodies and the like in mammals (e.g., mouse, rat, hamster, rabbit, cat, dog, bovine, sheep, monkey, human).

The negative symptoms of schizophrenia can be further subdivided into primary negative symptoms and secondary negative symptoms. The primary negative symptoms do not include symptoms better explained by side effects of drug therapy, post-psychotic depression or degeneracy. In one embodiment, the compound of the present invention is effective as a prophylactic or therapeutic drug for primary negative symptoms of schizophrenia or secondary negative symptoms of schizophrenia selected from the group selected from emotional flattening (emotional immobility, unresponsiveness, poor eye contact, limited body movement), alogia, demotivation, anhedonia, discomfort (depression, anxiety and anger), disturbance of sleep patterns (sleep in daytime, dysphoria/night-time activity), abnormal psychomotor activity (pacing, rocking, indifference), and lack of insight in mammals.

In one embodiment, the compound of the present invention is effective as a prophylactic or therapeutic drug for schizophrenia-associated disease, schizophrenia spectrum disorder, acute schizophrenia, chronic schizophrenia, NOS schizophrenia, schizophrenia affective disorder, schizophrenia-like disorder, paraphrenia, delusive personality disorder, schizoid personality disorder, schizophrenia personality disorder, delusive disorder, psychosis, disease with psychotic elements, psychotic disorder, short-term psychotic disorder, Alzheimer's disease psychosis, Parkinson's disease psychosis, shared psychotic disorder, paranoid, disorganized, catatonic, unspecified, and/or residual schizophrenia, and schizophrenia-like disorder in mammals.

Since the compound of the present invention has superior M1PAM activity, a superior prophylactic or therapeutic effect on the above-mentioned diseases can be expected.

Since the compound of the present invention has excellent properties as a pharmaceutical product such as low toxicity, few side effects and the like, it can be safely administered orally or parenterally to mammals. "Parenteral" includes intravenous, intramuscular, subcutaneous, intraorgan, intranasal, intradermal, instillation, intracerebral, intrarectal, vaginal, intraperitoneal and intratumor administrations, administration to the vicinity of tumor and the like and direct administration to the lesion.

The dose of the compound of the present invention varies depending on the administration subject, administration route, and symptoms and is not particularly limited. For example, when orally administered to an adult patient with Alzheimer's disease (body weight 40-80 kg, for example, 60 kg), the dose of the compound is, for example, 0.001-1,000 mg/kg body weight/day, preferably 0.01-100 mg/kg body weight/day, preferably 0.1-10 mg/kg body weight/day. In another embodiment, for example, it is 0.01-1,000 mg, preferably 0.1-200 mg, more preferably 1-20 mg, per day. This amount can be administered in one to 3 portions per day.

In a medicament containing the compound of the present invention (sometimes to be abbreviated as "medicament of the present invention" in the present DESCRIPTION), the compound of the present invention can be used alone or as a pharmaceutical composition in which the compound is mixed with a pharmacologically acceptable carrier according to a method known per se as a method for producing a pharmaceutical preparation (e.g., the method described in the Japanese Pharmacopoeia). The medicament of the present invention can be safely administered orally or parenterally (e.g., intravenously, intramuscular, subcutaneous, intraorgan, intranasal, intradermal, instillation, intracerebral, intrarectal, vaginal, intraperitoneal, lesion etc.) as a pharmaceutical composition such as tablet (including sugar-coated tablet, film-coated tablet, sublingual tablet, orally disintegrating tablet, buccal tablet and the like), pill, powder, granule, capsule (including soft capsule, microcapsule), troche, syrup, liquid, emulsion, suspension, controlled-release preparation (e.g., immediate-release preparation, sustained-release preparation, sustained-release microcapsule), aerosol, films (e.g., orally disintegrable film, oral mucosa adhesive film), injection (e.g., subcutaneous injection, intravenous injection, intramuscular injection, intraperitoneal injection), drip transfusion, transdermal absorption type preparation, ointment, lotion, adhesive preparation, suppository (e.g., rectal suppository, vaginal suppository), pellet, nasal preparations, pulmonary preparation (inhalant), eye drop and the like.

As the aforementioned "pharmacologically acceptable carrier", various organic or inorganic carriers conventionally used as preparation materials (starting materials) can be used. For example, excipient, lubricant, binder, disintegrant and the like are used for solid preparations; solvent, solubilizer, suspending agent, isotonizing agent, buffer, soothing agent and the like are used for liquid preparations. Where necessary, a preparation additive such as a preservative, an antioxidant, a colorant, a sweetener and the like can also be used.

Examples of the excipient include lactose, sucrose, D-mannitol, starch, cornstarch, crystalline cellulose and light anhydrous silicic acid.

Examples of the lubricant include magnesium stearate, calcium stearate, talc and colloidal silica.

Examples of the binder include crystalline cellulose, sucrose, D-mannitol, dextrin, hydroxypropylcellulose, hydroxypropylmethylcellulose, polyvinylpyrrolidone, starch, sucrose, gelatin, methylcellulose and sodium carboxymethylcellulose.

Examples of the disintegrant include starch, carboxymethylcellulose, calcium carboxymethylcellulose, sodium carboxymethyl starch and L-hydroxypropylcellulose.

Examples of the solvent include water for injection, alcohol, propylene glycol, macrogol, sesame oil, corn oil and olive oil.

Examples of the solubilizing agent include polyethylene glycol, propylene glycol, D-mannitol, benzyl benzoate, ethanol, trisaminomethane, cholesterol, triethanolamine, sodium carbonate and sodium citrate.

Examples of the suspending agent include surfactants such as stearyltriethanolamine, sodium lauryl sulfate, lauryl aminopropionic acid, lecithin, benzalkonium chloride, benzethonium chloride, glycerol monostearate and the like; and hydrophilic polymers such as poly(vinyl alcohol), polyvinylpyrrolidone, sodium carboxymethylcellulose, methylcellulose, hydroxymethylcellulose, hydroxyethylcellulose, hydroxypropylcellulose and the like.

Examples of the isotonicity agent include glucose, D-sorbitol, sodium chloride, glycerol and D-mannitol.

Examples of the buffering agent include buffers such as phosphate, acetate, carbonate, citrate and the like.

Examples of the soothing agent include benzyl alcohol.

Examples of the preservative include paraoxybenzoates, chlorobutanol, benzyl alcohol, phenylethyl alcohol, dehydroacetic acid and sorbic acid.

Examples of the antioxidant include sulfite, ascorbic acid and α-tocopherol.

The content of the compound of the present invention in the medicament of the present invention is generally 0.01-100% (w/w), preferably 0.1-95% (w/w).

The compound of the present invention is simultaneously expected to show a cholinergic side effect reducing effect due to the low α value in addition to the prophylactic or therapeutic effect on the above-mentioned diseases.

The compound of the present invention is used in combination with an acetylcholinesterase inhibitor. Preferable examples of the acetylcholinesterase inhibitor include donepezil (including donepezil hydrochloride), rivastigmine and galanthamine. More preferred are donepezil (including donepezil hydrochloride) and rivastigmine. Further preferred is donepezil (including donepezil hydrochloride). In the following, the combined use of the compound of the present invention and an acetylcholinesterase inhibitor is referred to as "combined use in the present invention".

In the combined use in the present invention, the dose of the acetylcholinesterase inhibitor can be reduced compared to a dose thereof alone.

In the combined use in the present invention, a superior prophylactic or therapeutic effect on the above-mentioned diseases is obtained compared to use of the compound of the present invention or the acetylcholinesterase inhibitor alone. Such effect exceeds the additive effect of the both medicaments, and is a synergistic effect.

In the combined use in the present invention, the effect can be sufficiently obtained even at a small dose that cannot afford the prophylactic or therapeutic effect on the above-mentioned diseases when the compound of the present invention or acetylcholinesterase inhibitor alone is used. That is, the efficacy dose of the both medicaments can be substantially reduced by the combined use in the present invention.

Furthermore, cholinergic side effects developed in patients during (or after) administration of an acetylcholinesterase inhibitor in the treatment of diseases such as Alzheimer's disease and the like can be reduced by the decreased dose of the acetylcholinesterase inhibitor and the superior synergistic effect afforded by the aforementioned combined use. Alternatively, the occurrence of cholinergic side effects can also be suppressed in patients who may have cholinergic side effects due to administration of an acetylcholinesterase inhibitor in the future.

In the combined use in the present invention, the compound of the present invention and an acetylcholinesterase inhibitor may be administered simultaneously or at different times to the subject of administration. In a preferable embodiment of the combined use in the present invention, an acetylcholinesterase inhibitor is administered to a mammal (preferably human) and then the compound of the present invention is administered to the mammal. In a further preferable embodiment of the combined use in the present invention, an acetylcholinesterase inhibitor is administered to a mammal (preferably human) and then the compound of the present invention is administered to the mammal after development (or observation) of cholinergic side effects (preferably diarrhea).

The administration mode in the combined use of the present invention is not particularly limited, and the compound of the present invention and the acetylcholinesterase inhibitor only need to be combined at the time of administration. Examples of such administration mode include: (1) administration of a single preparation obtained by simultaneously processing the compound and the acetylcholinesterase inhibitor, (2) simultaneous administration of two kinds of preparations of the compound and the acetylcholinesterase inhibitor, which have been separately produced, by the same administration route, (3) administration of two kinds of preparations of the compound and the acetylcholinesterase inhibitor, which have been separately produced, by the same administration route in a staggered manner, (4) simultaneous administration of two kinds of preparations of the compound and the acetylcholinesterase inhibitor, which have been separately produced, by different administration routes, (5) administration of two kinds of preparations of the compound and the acetylcholinesterase inhibitor, which have been separately produced, by different administration routes in a staggered manner (for example, administration in the order of the compound of the present invention; and the acetylcholinesterase inhibitor, or in the reverse order) and the like.

In the combined use in the present invention, a pharmaceutical composition of the mix of compound of the present invention or(and) an acetylcholinesterase inhibitor and a pharmacologically acceptable carrier can be used, like the medicament of the present invention.

The dose of the acetylcholinesterase inhibitor can be appropriately determined based on the clinically-used doses. The dose of the compound of the present invention varies depending on the administration subject, administration route, and symptoms and is not particularly limited. For example, when orally administered to an adult patient with Alzheimer's disease (adult, body weight 40-80 kg, for example, 60 kg), the dose of the compound is, for example, 0.001-1,000 mg/kg body weight/day, preferably 0.01-100 mg/kg body weight/day, preferably 0.1-10 mg/kg body weight/day. In another embodiment, for example, it is 0.01-1,000 mg, preferably 0.1-160 mg, more preferably 0.3-15 mg, per day. It is 0.3-23 mg per day for donepezil. It is 0.3-18 mg per day for rivastigmine. It is 0.3-24 mg per day for galanthamine. This amount can be administered in one to 3 portions per day.

The mixing ratio of the compound of the present invention and the acetylcholinesterase inhibitor can be appropriately determined according to the subject of administration, administration route, target disease, symptom, combination and the like.

EXAMPLE

The present invention is more completely understood by reference to the following Examples that provide examples of non-limiting embodiments of the present invention.

Example 1: Animal

Male ICR mice were supplied by CLEA Japan Inc. (Tokyo, Japan), and were used at 6-17 weeks of age. C57BL/6-Chrm-1tml Stl/J WT mice and KO mice were obtained from Massachusetts Institute of Technology (Cambridge, MA), and used at 8 months old. These animals were used for experiments after at least 1 week of acclimation. All mice were housed in a light controlled room (12-h light/dark cycle with lights on at 7:00). Food and water were provided at libitum.

Example 2: Reagent

[$^3$H]-Pirenzepine was obtained from PerkinElmer (Waltham, MA). Other reagents used in the experiments were purchased from Tocris Bioscience (Minneapolis, MN) unless otherwise indicated. M1PAM (7-(((1S,2S)-2-hydroxycyclohexyl)oxy)-2-(4-(1-methyl-1H-pyrazol-3-yl)benzyl)isoindolin-1-one (hereinafter sometimes to be abbreviated as "compound A" in the present specification), 3-fluoro-2-((2-(4-(1-methyl-1H-pyrazol-4-yl)benzyl)-3-oxo-2,3-dihydro-1H-isoindol-4-yl)oxy)benzonitrile (hereinafter sometimes to be abbreviated as "compound B" in the present specification), 3-((1S,2S)-2-hydroxycyclohexyl)-6-((6-(1-methyl-1H-pyrazol-4-yl)pyridin-3-yl)methyl)benzo[h]quinazoline-4(3H)-one (hereinafter sometimes to be abbreviated as "compound C" in the present specification), 2-(2-fluorophenyl)-5-(4-(1H-pyrazol-1-yl)benzyl)-2,5-dihydro-3H-pyrazolo[4,3-c]quinolin-3-one (hereinafter sometimes to be abbreviated as "compound E" in the present specification), 2-(4-(1-methyl-1H-pyrazol-4-yl)benzyl)-7-(2-(piperidin-1-yl)ethoxy)isoindolin-1-one (hereinafter sometimes to be abbreviated as "compound F" in the present specification) and 2-(4-(1-methyl-1H-pyrazol-4-yl)benzyl)-7-(1H-pyrazol-5-yl)isoindolin-1-one (hereinafter sometimes to be abbreviated as "compound G" in the present specification)) were suspended in 0.5% (w/v) methylcellulose (MC) in distilled water and administered orally. Scopolamine hydrobromide was dissolved in saline and administered subcutaneously. All compounds used in in vivo experiments were administered to mice at a dose of 10 or 20 mL/kg body weight. In an in vitro Magnus assay, the compounds were dissolved in dimethyl sulfoxide (DMSO). Compound A, compound B, compound F and compound G can be produced according to the production method, Reference Example and Example described in WO 2014/077401 or a method analogous thereto. Compound C can be produced according to the Reference Example and Example described in WO 2010/059773 or a method analogous thereto. Compound E can be produced according to the Reference Example and Example described in WO 2011/049731 or a method analogous thereto.

Example 3: Magnus Assay

After overnight fasting, mice were sacrificed by decapitation. The ileum was quickly dissected out and suspended in ice-cold Krebs solution with the following composition (in mM): NaCl, 120.7; KCl, 5.9; $CaCl_2$, 2.5; $MgCl_2$, 1.2; $NaHCO_2$, 15.5; $NaH_2PO_4$, 1.2; and glucose, 11.5. Longitudinal segments of ileum (10-15 mm long) were detached of mesentery and adipose tissue, and mounted in organ baths containing 10 mL of Krebs solution aerated with 95% $O_2$/5% $CO_2$. Bath temperature was maintained at 37° C. The isolated ileum was given a passive load of 0.5 g. The contractile response of the isolated ileum was continuously recorded with isometric transducer (MLT050/A, ADInstruments, New South Wales, Australia) and recorder (PowerLab 8/30 ML870 and Octal Bridge Amp ML228, ADInstruments).

Platinum electrodes (3-20 mm apart, Iwashiya Kishimoto Medical Instruments, Kyoto, Japan) were mounted on both sides of the isolated ileum. The electrodes were connected to an electric stimulator (SEG-3104, Nihon Kohden, Tokyo, Japan) and an amplifier (SIG-3140, Nihon Kohden) for EFS with square wave pulses (20 V over the electrodes, 50 ms duration, and 20 Hz frequency); pulse trains were lasting for 10 s with 20 s pause.

The EFS produced sustained tonic contraction, followed by relaxation. The contraction was measured as the maximum strength from the baseline. The effects of experimental substances on the maximum contraction were measured. At the beginning of each experiment, a series of control EFS cycles was tested for more than 1 h to observe stability of contractile response. The ileum with a steady contractile response elicited by control EFS during the 1 h was used to investigate the effect of test compounds.

After responses to control EFS reached a steady-state, the compounds were added to the Magnus bath cumulatively, without washing between the subsequent doses. The interval between two adjacent doses was always at least 5 min, thus the isolated preparations receive at least 10 pulses in each dose of the compounds. After cumulating all doses of compounds, the bath was washed three times, and the ilea were allowed to rest for further 30 min. The effect of each concentration of the compounds on ileum contraction induced by EFS was calculated from the average value of 10 responses of the maximum strength. Then the ileum contractile response was expressed as a ratio (%) of the mean maximum contraction to that obtained with the pre-treated DMSO (solvent) to obtain concentration-response curve. Due to very small size of relaxations, the effects of the compounds on them was not be analyzed.

Example 4: Binding Assay

Binding assay was performed in 96-well plate format. Cell membranes from FreeStyle 293 cells transiently expressed human M1R were incubated with test compounds, ACh and 4 nM [$^3$H]-pirenzepine in an assay buffer (20 mM HEPES, 100 mM NaCl, 10 mM $MgCl_2$, 0.1% fatty acid free BSA). After 2 h incubation at room temperature, cell membranes were transferred to GF/C filter plates (PerkinElmer, Massachusetts, USA) using cell-harvester (PerkinElmer) and washed 5 times with 300 μL of 50 mM Tris-HCl. Then, GF/C plates were dried at 42° C. 25 μL of microscint 0 (PerkinElmer) was added and the radioactivity was measured by Topcount (PerkinElmer). Non-specific bound was defined in the presence of 10 μM atropine.

Example 5: $Ca^{2+}$ Flux Assay in Experiment

Chinese hamster ovary (CHO-K1) cells stably expressing human M1Rs (hM1R-CHO) were plated in black-walled clear-bottomed 384-well plates (5,000 cells/well) and cultured overnight at 37° C. in the presence of 5% $CO_2$ in Ham's F-12 medium supplemented with 10% FBS and 100 U/mL penicillin-streptomycin. The following day, the medium was removed and incubated with assay buffer (Hank's balanced salt solution with 20 mM HEPES, 0.1% fatty acid free BSA) containing 2.5 μg/mL Fluo-4 AM and 1.25 mM probenecid for 30 min at 37° C. in the presence of 5% $CO_2$. After 30 min incubation at room temperature, cells were stimulated with compounds. In this experiment, ACh and each PAM were added to the cells simultaneously. Calcium flux was measured using a fluorescence imaging plate reader (FLIPR) tetra system (Molecular Devices, Sunnyvale, CA).

Example 6: Assessment of Diarrhea in Detail

On the day of the experiment, mice were randomly divided into four groups (n=6-9). Mice were transferred to the individual cages and allowed to acclimate for more than 1 h. Each mouse was treated with either vehicle (10 or 20 mL/kg) or a single dose of each compound, including Compound A (3, 10 or 30 mg/kg p.o.), Compound B (10, 30, 100, 300 or 1,000 mg/kg p.o.) or Compound C (10 mg/kg p.o.). The animals were monitored, and scored the severity of diarrhea at 0.5, 1, 2, 4 and 6 h after administration. The diarrhea was assessed using an arbitrary scoring scale ranging from 0 to 3: 0=normal pellets; 1=wet but formed feces; 2=swollen or mucous feces; 3=severe watery diarrhea. The highest score during the observation was adopted.

Example 7: Quantitative Reverse Transcription-Polymerase Chain Reaction (RT-PCR) Analysis For in vivo pharmacodynamics (PD) marker analysis, mice were sacrificed by decapitation at 90 min after administration of Compound A or Compound B. Hippocampal tissues were isolated from the brain. These tissues were stored at −80° C. until RNA extraction. Total RNA from individual tissues was extracted using QIAzol Lysis Reagent and the RNeasy kit (Quiagen, Hilden, Germany) following the manufacturer's instruction. RT-PCR was carried out using ABI PRISM 7900HT sequence detection system (Life Technologies, Bedford, MA) and TagMan reagents (Eurogentec, Seraing, Belgium). RNA quantities were normalized using glyceraldehyde-3-phosphate dehydrogenase (GAPDH) mRNA transcripts according to manufacturer's instruction. The following primers were used for mouse Arc analysis: forward primer, 5'-AGCTGAAGC-CACAAATGCAG-3' (SEQ ID NO:3); reverse primer, 5'-CTGAGTCACGGAGCTGAGC-3' (SEQ ID NO:4), Tag-Man probe, 5'-AGACCTGACATCCTGGCACCTCCTGG-3' (SEQ ID NO:5). The primers used for mouse Gapdh analysis were TagMan Rodent GAPDH Control Reagent, VIC probe, purchased from ABI (Applied biosystems-Life Technologies, Waltham, MA).

Example 8: Y-Maze Task in Mice

The Y-maze apparatus has a three-arm maze with equal angles between all arms and made of black colored acrylic. Each arm consisted of 40 cm length, 4 cm width, and 12 cm walls. The Y-maze was located in a sound-attenuated room and illuminated at 10 lux. Compound B (10 or 30 mg/kg) and Compound A (1, 3 or 10 mg/kg) were pretreated orally at 60 min prior to the testing. After 30 min, memory impairment was induced by administering scopolamine (0.3 or 1 mg/kg, as hydrobromide salt, s.c.). At 30 min after the administration of scopolamine, mice were placed in the Y-maze and then spontaneous alternation performance was assessed visually for 5 to 8 min. Each animal underwent one trial. A mouse was considered to have entered an arm when all four paws were positioned in one third of the arm runway from the center of the Y maze. Alternations were defined as successive entries into each of the three arms on overlapping triplet sets, and alternation rate, expressed as a percentage, referred to the ratio of actual (total alternations) to possible alternations (total arm entries−2)×100. Mice were excluded from the analyses if they possessed low exploratory activity defined as fewer than 10 total arm entries. The dose of scopolamine was regulated so that the alternation ratio significantly decreased.

Example 9: Data Analysis

All data were analyzed using GraphPad Prism 5 software (GraphPad Software Inc., California, USA). Radioligand binding data were globally fitted to the following allosteric ternary complex model:

$$Y = \frac{\frac{[C]}{K_C} + \frac{\alpha_{BC}[B][C]}{K_B K_C}}{1 + \frac{[A]}{K_A} + \frac{[B]}{K_B} + \frac{[C]}{K_C} + \frac{\alpha_{AB}[A][B]}{K_A K_B} + \frac{\alpha_{BC}[B][C]}{K_B K_C}}$$

where Y is the percentage of specific binding; [A], [B], and [C] are the concentrations of ACh, the allosteric modulator, and [$^3$H]-pirenzepine, respectively; $K_A$, $K_B$, and $K_C$ denote the equilibrium dissociation constants of ACh, the allosteric modulator, and [$^3$H]-pirenzepine, respectively; and $\alpha_{AB}$ and OBC are the cooperativities between the allosteric modulator and ACh or [$^3$H]-pirenzepine, respectively. Values of cooperativity greater than 1 denote positive cooperativity (allosteric enhancement of orthosteric ligand binding), whereas values of cooperativity less than 1 denote negative cooperativity (allosteric inhibition of orthosteric ligand binding). The functional interactions between M1 PAMs and ACh were globally fitted to the following operational model of allosterism (Nat Rev Drug Discov. 2009; 8(1): 41-54 and Trends Pharmacol Sci. 2007; 28(8): 382-9)

$$E = \frac{E_{max}(\tau_A[A](K_B + \alpha\beta[B]) + \tau_B[B]K_A)^n}{([A]K_B + K_AK_B + K_A[B] + \alpha[A][B])^n + (\tau_A[A](K_B + \alpha\beta[B]) + \tau_B[B]K_A)^n}$$

the pharmacological effect and Emax denotes the maximum possible effect; [A] and [B] are the concentrations of ACh and PAM, respectively; $K_A$ and $K_B$ denote the equilibrium dissociation constants of ACh and PAM, respectively; $\tau_A$ and $\tau_B$ represent the operational measures of ACh and PAM efficacy, respectively; a is the binding cooperativity between ACh and PAM (activity to enhance ACh affinity to M1R); β is the magnitude of the allosteric effect of PAM on the signaling efficacy of ACh; n denotes the slope factor. For the analysis of functional data, the equilibrium dissociation constant of each PAM and the cooperativity between ACh and each PAM were fixed to those determined from the binding experiments.

Example 10: Statistics

Experimental results were expressed as the mean±standard error of the mean (S.E.M.). The statistical significance of differences between two groups was assessed by Aspin-Welch's t-test at a level 0.05. In the experiments that examined the effects of multiple doses of test compounds, the effects were analyzed using Bartlett's test, which was used for testing the homogeneity of variance, followed by two-tailed Williams' test (for parametric data, P>0.05 by Bartlett's test) or two-tailed Shirley-Williams test (for non-parametric data, P≤0.05 by Bartlett's test). Data were analyzed using EXSUS (Ver.8.0.0, CAC EXICARE Corporation, Tokyo, Japan) and statistical significance was set at P≤0.05.

Example 11: Effects of Compound C on Diarrhea in Wild-Type (WT) and M1R Knock-Out (KO) Mice To determine whether M1R activation by M1PAM caused diarrhea, a M1 selective PAM Compound C was administered orally to both WT and M1R KO mice. Compound C at 10 mg/kg induced diarrhea in WT mice, but not in M1R KO mice (FIG. 1). Thus, M1PAMs including Compound C would induce diarrhea through M1R activation in rodents.

Example 12: Relationship Between the Ileum Contraction and M1 PAM Parameters

The extracellular environment such as ACh concentration around M1R might be different between the brain and peripheral tissues, and each M1 PAM with different characteristics can exert distinct effects from tissue to tissue in the body. Thus, it was decided to explore key M1R modulation parameters associated with the ileum contraction. At first, 7 M1 PAMs with ≥100-fold selectivity over other muscarinic subtypes were selected for in vitro functional analyses (Table 1). Then, various M1 PAM parameters of these M1 PAMs were assessed by using the in vitro binding modulation assay (Table 1-2). Next, the effects of these compounds on ileum contractile response by using the Magnus assay were examined. The ileum contraction levels extended from 93 to 116% compared with control condition (Table 2). The correlation between the ileum contractile response and the various M1 PAM parameters was explored. The results of a Pearson's correlation analysis between the pIP, log α, or log β, and the ileum contraction augmentation at 1 μM are shown in FIG. 2. Both the pIP and log β did not show the correlation with the augmented level of ileum contraction (FIG. 2A, r=0.4979, P=0.2555, FIG. 2C, r=−0.5505, P=0.2004). Interestingly, log α, was significantly correlated with the ileum contractile responses with correlation coefficient greater than 0.80 (FIG. 2B, r=0.8075, P=0.0281).

TABLE 1

Functional parameters, agonistic and PAM activity, and selectivity for M1R, of M1 PAMs

| | M1 agonist activity | | M1PAM activity | | PAM activity against other muscarinic receptor subtypes | | | |
|---|---|---|---|---|---|---|---|---|
| | $pEC_{50}$ | | pIP | | M2R | M3R | M4R | M5R |
| Compound | Mean | SEM | Mean | SEM | pIP | pIP | pIP | pIP |
| Compound A | 7.14 | 0.20 | 7.99 | 0.09 | <5.00 | <5.00 | 6.00 | <5.00 |
| Compound B | 6.17 | 0.10 | 7.39 | 0.08 | <5.00 | <5.00 | <5.00 | <5.00 |
| Compound C | 8.79 | 0.24 | 8.68 | 0.19 | <5.00 | <5.00 | <5.00 | <5.00 |
| Compound E | 6.66 | 0.19 | 8.07 | 0.11 | <5.00 | <5.00 | <5.00 | <5.00 |
| Compound F | 5.68 | 0.32 | 7.10 | 0.10 | <5.00 | <5.00 | <5.00 | <5.00 |
| Compound G | <5.00 | N/A | 6.56 | 0.19 | <5.00 | <5.00 | <5.00 | <5.00 |

EC50, eliciting 50% of the maximal response of an endogenous ligand, ACh, reflects the agonistic activity for M1R under conditions without ACh. Inflection point (IP) reflects the PAM potency for M1-M5R upon application of M1 PAM in the presence of a low concentration of ACh, eliciting 20% of the maximal ACh response (EC20). Results of the in vitro functional parameters for M1R represent the mean and S.E.M. of three independent experiments. N/A stands for "not available". PAM means positive allosteric modulator (Table 1).

TABLE 2

Binding parameters of M1 PAMs, and ileum contractile response at 1 μM in the in vitro Magnus assay

| | M1PAM parameters | | | | | | | | Magnus assay Ileum contraction at 1 μM | |
|---|---|---|---|---|---|---|---|---|---|---|
| | log α | | log β | | $pK_B$ | | Log $T_B$ | | (% of cont.) | |
| Compound | Mean | SEM | Mean | SEM | Mean | SEM | Mean | SEM | Mean | SEM |
| Compound A | 3.30 | 0.20 | 0.13 | 0.06 | 4.58 | 0.23 | 2.06 | 0.23 | 116 | 6.3 |
| Compound B | 1.18 | 0.09 | 0.58 | 0.07 | 6.01 | 0.14 | −0.10 | 0.01 | 97 | 2.1 |
| Compound C | 3.25 | 0.04 | −0.39 | 0.02 | 6.54 | 0.03 | 1.49 | 0.03 | 104 | 3.5 |
| Compound E | 2.67 | 0.16 | −0.23 | 0.03 | 5.51 | 0.12 | 0.65 | 0.09 | 106 | 6.5 |
| Compound F | 1.54 | 0.01 | 0.87 | 0.05 | 5.04 | 0.04 | 0.15 | 0.01 | 102 | 2.1 |
| Compound G | 0.56 | 0.13 | 0.85 | 0.04 | 4.83 | 0.21 | N/A | N/A | 93 | 2.4 |

Allosteric effects of M1 PAM on the binding and signaling of the orthosteric ligand were reflected by α- and β-values, respectively. $K_B$-value means the affinity of the PAM to the free M1R. $\tau_B$ represents intrinsic agonistic efficacy in the system. In the Magnus assay, the augmentation of ileum contraction by PAM treatment (1 μM) in isolated mouse ileum with EFS was described. Results of the in vitro binding parameters represent the mean and S.E.M. of three independent experiments. Results of the in vitro Magnus assay represent the mean and S.E.M. n=3-11 per group. N/A stands for "not available" (Table 2)

Example 13: Effect of a Low α-Value Compound (Compound B) on Cognition and Diarrhea in Mice To assess the detailed profiles of an M1 PAM with lower α-value, Compound B with log α of 1.18 (α=16) was selected as a representative compound (FIG. 3A, Table 2). Compound B at up to 1 μM had no effect on the EFS-induced ileum contraction (FIG. 3B). As expected from this result, Compound B at up to 1000 mg/kg did not induce severe diarrhea (FIG. 3C-D); note that this compound has lack of PK linearity at higher dosages, and its plasma concentration at 1000 mg/kg was 3.6-fold higher than that at 30 mg/kg (Table 3). To guide the selection of the dosage for cognitive task, induction of Arc mRNA expression was used as a PD marker for M1R activation; BQCA has been reported to increase Arc mRNA expression level in the brain through M1R activation (Proceedings of the National Academy of Science of the United States of America. 2009; 106(37): 15950-5). Compound B at 10-100 mg/kg showed about 2-fold increase in Arc mRNA expression level in mouse hippocampus (FIG. 3E). From this result, the dose of 10 and 30 mg/kg were selected for the evaluation of drug efficacy for scopolamine-induced cognitive deficits in mice. Compound B at 30 mg/kg significantly ameliorated scopolamine-induced cognitive deficits in Y-maze task in mice under conditions of 5-min measurement (FIG. 3F). Thus, the M1 PAM with low α-value could improve cognitive deficits without any signs of diarrhea.

TABLE 3

Pharmacokinetic parameters after oral administration to mice

| | Compound B | |
|---|---|---|
| PK parameter | 30 mg/kg | 1000 mg/kg |
| Cmax (μg/mL) | 0.27 | 0.97 |
| Tmax (h) | 2.0 | 1.7 |
| $AUC_{0-4\,h}$ (μg · h/mL) | 0.80 | 3.02 |

Plasma concentration of Compound B at 30 and 1000 mg/kg. Plasma samples were collected at 0.5, 1, 2, 4 and 6 h after oral treatment. Results represent the mean. n=3 per group.

Example 14: Effect of a High α-Value Compound (Compound A) on Cognition and Diarrhea Induction in Mice (Comparative Example)

Next, Compound A (FIG. 4A) was selected as a representative high α-value compound; Compound A has a log α of 3.30 (α=2371) (Table 2). As expected, Compound A (0.1 nM-1 μM) caused concentration-dependent augmentation of the EFS-induced ileum contraction in vitro Magnus assay, and this enhancement was suppressed by 1 nM of telenzepine (FIG. 4B). In line with this observation, Compound A at 10 and 30 mg/kg caused severe diarrhea in mice (FIG. 4C). Compound A enhanced the expression level of Arc mRNA in a dose-dependent manner, and showed significant increase at 30 mg/kg in mice (FIG. 4D). Then, cognitive improvement was assessed using scopolamine-induced cognitive deficits in Y-maze task in mice. Under conditions of 5-min measurement, scopolamine did not cause significant reduction of spontaneous alternation ratio, and Compound A at 10 mg/kg showed trends to improve the scopolamine-induced cognitive deficits (FIG. 4E). When prolonging the measurement time to 8 min, scopolamine treatment induced prominent cognitive deficits, and Compound A at 10 mg/kg significantly ameliorated the scopolamine-induced decrease in spontaneous alternation ratio in Y-maze task in mice (FIG. 4F).

Example 15: Animals

Male Long Evans rats (Japan SLC Inc., Hamamatsu, Japan) were used for in vivo IP1 assay and novel object recognition task. For the assessment of side effects, male Sprague-Dawley rats were purchased from Charles River Laboratories Japan, Inc. (Yokohama, Japan). All rats were used at 6-9 weeks of age. Male ICR mice (Japan CLEA Inc., Tokyo, Japan) at 7-9 weeks were used for in vitro Magnus assay. Male C57BL/6J mice (Japan CLEA Inc.) at 4-10 weeks were used for electrophysiology. C57BL/6-Chrm-1tm1 Stl/J wild-type mice and M1R KO mice were obtained from Massachusetts Institute of Technology (Cambridge, MA), and used at 8 months old. All animals were group-housed in a temperature- and humidity-controlled room with a 12 h dark/light cycle with lights on at 7:00. Food and water were provided ad libitum. All animals were acclimated to the facility for at least 1 week prior to use. The care and use of the animals and the experimental protocols used in this research were approved by the Experimental Animal Care and Use Committee of Takeda Pharmaceutical Company Limited.

Example 16: Chemicals

Compound C and 4-fluoro-2-[(3S,4S)-4-hydroxytetrahydro-2H-pyran-3-yl]-5-methyl-6-[4-(1H-pyrazol-1-yl)benzyl]-2,3-dihydro-1H-isoindol-1-one (hereinafter sometimes to be abbreviated as "compound D" in the present DESCRIPTION) were synthesized by Takeda Pharmaceutical Company Limited. Donepezil hydrochloride was purchased from Mega Fine Pharma (P) Limited (Mumbai, India). Scopolamine hydrobromide was purchased from Tocris Bioscience (Ellisville, MO). Lithium chloride (LiCl) was obtained from Wako Pure Chemical Industries Limited (Osaka, Japan). Compound D was suspended in 0.5% (w/v) methylcellulose in distilled water and donepezil hydrochloride was dissolved in distilled water and both of them were injected per orally (p.o.). Scopolamine hydrobromide, and LiCl were dissolved in saline and injected subcutaneously (s.c.). Doses of donepezil and scopolamine are expressed as the respective salts. Compounds used in vivo studies were dosed in a volume of 2 mL/kg body weight for rats, and 10 mL/kg body weight for mice, respectively. In vitro Magnus method and in vitro electrophysiology study, compounds were dissolved in dimethyl sulfoxide (DMSO). Compound D can be produced according to Reference Example and Example described in WO2016/208775 or method based thereon.

Example 17: $Ca^{2+}$ Flux Assay

CHO-K1 cells expressing human M1 receptors were plated on a 96-well black clear bottom plate (Corning, New York, NY) at 30,000 cells/well, and cultured at 37° C. and 5% $CO_2$ for 1 day. The medium was removed and the cells were incubated with calcium dye buffer (HBSS (Life Technologies, Carlsbad, CA), 20 mM HEPES (Life Technologies), 0.1% fatty acid-free BSA (Wako), 0.08% pluronic F127 (Dojindo Laboratories, Kumamoto, Japan), 2.5 µg/mL Fluo-4 (Dojindo Laboratories), 1.25 mM probenecid (Dojindo Laboratories)) for 30 min at 37° C. and 5% $CO_2$. After 30 min incubation at room temperature, the cells were stimulated with various concentrations of test compounds dissolved in assay buffer (HBSS (Life Technologies), 20 mM HEPES (Life Technologies), 0.1% fatty acid-free BSA (Wako)) containing EC20 concentrations (0.8-1 nM) of ACh and $Ca^{2+}$ response was measured using CeilLux (PerkinElmer). For determination of positive allosteric modulation activity of M1PAMs, the response to $EC_{20}$ ACh was set as the 0% response and the response to 10 µM ACh was set as the 100% response. The potency of M1PAMs was shown as the value of inflection point (IP). IP value and 95% confidence intervals were calculated by XLfit of GraphPad Prism 5 Software (GraphPad Software Inc., LaJolla, CA, USA) from the data expressed as % of control.

Example 18: In Vivo Inositol Monophosphate (IP1) Assay Procedure

It was reported methods for measuring in vivo phosphoinositide hydrolysis with [$^3$H]-myo-inositol (Bymaster et al., Brain. Res. 1998 Jun. 8; 795(1-2):179-90; Patel and Freedman, Eur. J. Pharmacol. 1994 May 17; 267(3):329-34). To assess in vivo phosphoinositide hydrolysis more readily, a homogeneous time-resolved fluorescence (HTRF)-based assay system, IP-One HTRF® assay kit (Cisbio Bioassays, Codolet, France) (Trinquet et al., Anal Biochem. 2006 Nov. 1; 358(1):126-35) was developed.

Long Evans rat and C57BL/6J mouse were used for the assay. On the day of the experiment, animals were transferred to the individual cages and allowed to acclimate for at least 1 h and Compound D (3 mg/kg, p.o.), donepezil (3 mg/kg p.o.) and Compound C (10 mg/kg p.o.) were administered 3, 1.5, and 3 h prior to sacrifice, respectively. In all IP1 assay, 2 h after administration of Compound D or Compound C, LiCl (10 mmol/kg) was injected subcutaneously to inhibit degradation of IP1. One hour after the injection of LiCl, animals were killed by decapitation and their brains were removed and washed with cold saline containing 50 mM LiCl. Hippocampus was isolated from the brain. These tissues were quickly dissected, frozen on dry ice, weighed, and stored at -80° C. until analysis. Each tissue was homogenized with a Physcotron (Microtec Company Limited, Chiba, Japan) in 39 (for rats) or 19 (for mice) volumes of hippocampus tissue weight of homogenization buffer (10 mM HEPES pH 7.4, 50 mM LiCl, 150 mM NaCl, and 1% Triton X-100). The homogenate was incubated on a rotator for 1 h at 4° C. and then centrifuged at 12000 g for 20 min at 4° C. The supernatant was collected and diluted with 39 (for rats) or 19 (for mice) volumes of dilution buffer (10 mM HEPES pH 7.4, 50 mM LiCl, and 150 mM NaCl) to avoid matrix interference. The diluted supernatant was subjected to measurement of the IP1 and protein concentrations. The diluted supernatant (20 µl) was transferred into a 384-well Optiplate (PerkinElmer), followed by addition of d2-labeled IP1 (5 µl) and terbium cryptate-labeled anti-IP1 antibody (5 µl) diluted in lysis buffer provided in the kit. After incubation for at least 1 h at room temperature, the fluorescence intensities at 665 nm and 615 nm were measured using an EnVision multilabel reader (PerkinElmer). The IP1 concentration was calculated based on the HTRF ratio (fluorescence at 665 nm fluorescence at 615 nm×10$^4$). The protein concentration was determined by Pierce BCA protein assay kit (Thermo Scientific, Rockford, IL) according to the manufacturer's instructions. The in vivo IP1 level was calculated as the ratio of the concentration of IP1 to that of total protein, and then it was represented as % of vehicle-administered group (control group).

Example 19: In Vitro Ileum Contraction

After overnight fasting, mice were sacrificed. The ileum was quickly dissected out and suspended in ice-cold Krebs solution with the following composition (in mM): NaCl, 120.7; KCl, 5.9; $CaCl_2$, 2.5; $MgCl_2$, 1.2; $NaHCO_3$, 15.5; $NaH_2PO_4$, 1.2; and glucose, 11.5. Longitudinal segments of ileum (10-15 mm long) were detached of mesentery and adipose tissue, and mounted in organ baths containing 10 mL of Krebs solution aerated with 95% $O_2$/5% $CO_2$. Bath temperature was maintained at 37° C. The isolated ileum was given a passive load of 0.5 g. The contractile response of the isolated ileum was continuously recorded with isometric transducer (MLT050/A, ADInstruments, New South Wales, Australia) and recorder (PowerLab 8/30 ML870 and Octal Bridge Amp ML228, ADInstruments). Platinum electrodes (3-20 mm apart, Iwashiya Kishimoto Medical Instruments, Kyoto, Japan) were mounted on both sides of the isolated ileum.

The contraction was measured as the maximum strength from the baseline. The effects of experimental substances on the maximum contraction were measured. The ileum with a steady contractile response was used to investigate the effect of test compounds. The compounds were added to the organ bath cumulatively, without washing between the subsequent treatment concentration for a single compound. The interval between two adjacent treatment concentrations was always at least 3 min. After cumulating all treatments for a single compound, the bath was washed three times, and the isolated ilea were allowed to rest for further 30 min. The effect of each concentration of the compounds on ileum spontaneous contraction induced was calculated from the average value of 6 responses of the maximum strength. Then the ileum contractile response was expressed as a ratio of the mean maximum contraction to that obtained with the pre-treated DMSO (solvent). For the construction of concentration-response curve, normalized values of the ratio by DMSO treatment were used, which was expressed by percentages. Due to very small size of relaxations, the effects of the compounds on them was not be analyzed.

Example 20: Electrophysiology

Experiments were performed on coronal brain slices of the medial prefrontal cortex (mPFC) from 4-week-old male C57BL/6 mice. The animals were quickly sacrificed and the brain was placed in an ice-cold NMDG artificial cerebrospinal fluid (ACSF) (in mM): NMDG, 92; KCl, 2.5; $CaCl_2$, 0.5; $NaH_2PO_4$, 1.25; $MgSO_4$, 6; $NaHCO_3$, 30; glucose, 25; HEPES, 20; thiourea, 2; Na-ascorbate, 5; and Na-pyruvate, 3) (Ting J. T. et al., Methods Mol Biol. 2014; 1183:221-42). Slices were cut at a thickness of 300 μm with a vibroslicer. Slices were initially transferred to a holding chamber containing NMDG aCSF for 15 minutes at 34° C. Slices were then transferred to a room temperature holding chamber for at least 1 h containing HEPES aCSF (in mM): NMDG, 92; KCl, 2.5; $CaCl_2$, 2; $NaH_2PO_4$, 1.25; $MgSO_4$, 2; $NaHCO_3$, 30; glucose, 25; HEPES, 20; thiourea, 2; Na-ascorbate, 5; and Na-pyruvate, 3). Subsequently, the slices were transferred to the recording chamber, in which they were submerged and perfused with aCSF containing the following (in mM): NaCl, 124; KCl, 5; $NaH_2PO_4$, 1.2; $MgCl_2$, 1.5; $CaCl_2$, 2.5; glucose, 10; and $NaHCO_3$, 24), at a flow rate of 1-2 ml/min. All buffers were continuously bubbled and saturated with carbogen (95% $O_2$/5% $CO_2$). Current clamp recordings were carried out at 32-33° C. from visually identified pyramidal neurons from layer 5 using a borosilicate pipette (5-7 MΩ) filled with intracellular solution (in mM): K-gluconate, 135; KCl, 4; HEPES, 10; EGTA, 0.2; MgATP, 4; $Na_2GTP$, 0.3; pH 7.3 with KOH). Signals were acquired using a Multiclamp 700B amplifier and a Digidata 1440A interface board (Molecular Devices Japan, Tokyo, Japan), filtered between 2 kHz, sampled at 10 kHz, and analyzed with pClamp10 software.

Example 21: Novel Object Recognition Task (NORT) Procedure

On the day before testing, Long Evans rats were allowed to habituate to the behavioral test room environment for over 1 h, and then they were allowed to habituate to the empty test box (a gray-colored polyvinyl chloride box (40×40×50 cm)) for 10 min individually. Testing was comprised of two 3-min trials called the acquisition and the retention trials. These trials were separated by a given inter-trial interval (ITI). On the testing day, in the acquisition trial, rats were allowed to explore two identical objects (A1 and A2) for 3 min. In the retention trial, rats were again allowed to explore a familiar object (A3) and a novel object (B) for 3 min. The object exploration was defined as rats' licking, sniffing or touching the object with limbs while sniffing. Leaning against the object to look upward, standing or sitting on the object was excluded. The exploration time of each object (A1, A2, A3 and B) in each trial was measured manually. Novel discrimination index (NDI) was calculated using the following equation: novel object interaction/total interaction×100(%).

Effects of Monotherapy on Scopolamine-Induced Memory Deficits

The acquisition and the retention trials were separated by 4 h ITI. Compound D (0.03, 0.1, 0.3. 1, and 3 mg/kg p.o.), donepezil (0.1, 0.3, and 1 mg/kg p.o.), and Compound C (0.03, 0.3, and 3 mg/kg) were orally administered 2 h, 1 h, and 2 h prior to the acquisition trial, respectively. Scopolamine (0.1 mg/kg) was administered subcutaneously 30 min prior to the acquisition trial.

Effects of Combination of Compound D with Donepezil or Rivastigmine on Scopolamine-Induced Memory Deficits The acquisition and the retention trials were separated by 4 h ITI. In combination with donepezil or rivastigmine, donepezil (0.1 mg/kg p.o.) or rivastigmine (0.1 mg/kg, i.p.) was administered 1.5 h after administration of Compound D (0.1 mg/kg p.o.).

Effects of Combination of Compound C with Donepezil on Scopolamine-Induced Memory Deficits The acquisition and the retention trials were separated by 4 h ITI. In combination with donepezil, donepezil (0.1 mg/kg p.o.) was administered 1.5 h after administration of Compound C (0.1 mg/kg p.o.).

Example 22: Assessment of Cholinergic Side Effects

SD Rats were placed individually into observation cages and acclimated for at least 1 h. Each rat was treated with vehicle, donepezil (1, 3, 10, and 30 mg/kg, p.o.) alone, Compound D (1, 3, 10, and 30 mg/kg p.o.) alone, Compound C (0.01, 0.03, 0.1, and 0.3 mg/kg p.o.) alone, combination of Compound D (1 and 3 mg/kg p.o.) with donepezil (0.3 mg/kg p.o.) or combination of Compound D (0.1 mg/kg p.o.) with rivastigmine (0.1 mg/kg, i.p.), and then cholinergic side effects including diarrhea, convulsion, lacrimation, salivation, myosis, and fasciculation were assessed. The severity was scored by an observer blinded to group allocation at 0.5, 1, 2, 4, and 6 h post-dose for compound alone, at 10 and 30 min and 1, 2, 4, and 6 h post-dose of donepezil or rivastigmine for a combination study. The severity of diarrhea was scored as follows: 0, normal pellets; 1, wet but formed feces; 2, swollen or mucous feces; 3, severe watery diarrhea. For diarrhea, the number of rats and mice, in which more than or equal to 2 was scored, was counted. For fasciculation, the number of rats with marked fasciculation of both the upper and lower limbs was counted. For lacrimation, the number of rats, in which moderate to marked discharge (severer lacrimation than fluid around eyes) was induced, was counted. For salivation, the number of rats with severe salivation, but not just noticeably wet around mouth, was induced was counted. The maximum score during the observation was adopted.

Statistics

Experimental results were expressed as means+S.E.M. For dose-response studies, statistical comparison between vehicle- and drug-treated groups was made by one-tailed Williams' test or one-tailed Shirley-Williams test with P 0.025 taken to indicate a significant difference. Statistical analysis between two groups was performed by Student's t-test, and a P value of less than 0.05 was considered statistically significant. For combination studies with donepezil, Dunnett's or Steel's multiple comparison test was performed with statistical significance set at P≤0.05, where appropriate.

Example 23: Compound D Selectively Activates Human M1R with Low α-Value In Vitro and In Vivo First, M1PAM from a chemical library was screened using a $Ca^{2+}$ flux assay in a CHO-K1 cells expressing human M1R, then assessed M1R selectivity of the hit compounds. The potential of the selected compounds in the enhancement of binding affinity between ACh and M1R as indicated by α-value was assessed by the binding modulation assay. As a result, Compound D was discovered as a potent M1 selective PAM with a low α-value. An IP value of Compound D for human M1R was 2.7 nM when potentiating $EC_{20}$ ACh (FIG. 5A). M1R selectivity of Compound D over other human muscarinic receptor subtypes was not less than 3700-fold; IPs of Compound D for M2-M5R in the $Ca^{2+}$ flux assays using CHO-K1 cells expressing each human muscarinic receptor subtype were higher than 10000 nM (FIG. 5A). Binding modulation assay measuring the displacement of [$^3$H]-Pirenzepine from human M1R by ACh revealed that Compound D had an α-value of 199 (FIG. 5B). IP1 production by Compound D at 3 mg/kg in the hippocampus of wild-type and M1R KO mice was assessed. In wild-type mice, Compound D at 3 mg/kg significantly induced IP1 production in the hippocampus (153.3±9.3%, FIG. 5C). Importantly, Compound D at 3 mg/kg p.o. did not induce IP1 production in the hippocampus of M1R KO mice (FIG. 5C). No significant differences in PK profile were observed between wild-type and M1R KO mice (Table 4), thus, Compound D would induce IP1 production through M1R activation in mice.

TABLE 4

There is no significant difference in brain concentration of Compound D between wild-type and M1R KO mice.

| PK parameter | Compound D (3 mg/kg, p.o.) in wild-type mice | Compound D (3 mg/kg, p.o.) in M1KO mice |
| --- | --- | --- |
| Plasma concentration (μg/mL) | 3.11 ± 0.49 | 3.26 ± 0.26 |
| Brain concentration (μg/g) | 0.35 ± 0.08 | 0.37 ± 0.05 |

Plasma and brain concentration of Compound D in sample of in vivo IP1 assay at 3 h after oral treatment. Results represent the mean±SD. n=10 per group.

Example 24: Compound C Selectively Activates M1R with High α-Value In Vitro and In Vivo (Comparative Example)

To understand how α value affects the pharmacological profile of M1PAM, Compound C was characterized as a M1PAM with a similar IP value to that of Compound D and a higher α value than Compound D. Compound C had an α value of 1786 in binding modulation assay (FIG. 6C), and showed an IP value of 0.62 nM in vitro $Ca^{2+}$ functional assay using a CHO-K1 cells expressing human M1R. IPs of Compound C for M2-M5R in the $Ca^{2+}$ flux assays using CHO-K1 cells expressing each human muscarinic receptor subtype were higher than 1,000 nM (FIG. 6B). IP1 production by Compound C at 10 mg/kg in the hippocampus of wild-type and M1R KO mice was assessed. Compound C at 10 mg/kg, p.o. significantly induced IP1 production in hippocampus in wild-type mice, but not in M1R KO mice (FIG. 6D). No significant differences in brain concentration of Compound C were observed between wild-type and M1R KO mice (Table 5), thus, Compound C would induce IP1 production through M1R activation in mice.

TABLE 5

There is no significant difference in brain concentration of Compound C between wild-type and M1R KO mice.

| PK parameter | Compound C (10 mg/kg, p.o.) in wild-type mice | Compound C (10 mg/kg, p.o.) In M1KO mice |
| --- | --- | --- |
| Plasma concentration (ng/mL) | 2337 ± 628 | 6132 ± 1163 |
| Brain concentration (ng/g) | 63.7 ± 16.8 | 62.7 ± 9.1 |

Plasma and brain concentration of Compound C in sample of in vivo IP1 assay at 3 h after oral treatment. Results represent the mean±SD. n=10 per group.

Example 25: Compared to Compound C, a M1PAM with a High α Value, Compound D has Lower Impact on Ileum Motility in Magnus Method The effects of Compound D and Compound C on the ileum contraction were examined by using the in vitro Magnus assay. Compound C, but not Compound D, strengthened the spontaneous ileum motility in a concentration-dependent manner (FIG. 7). Thus, compared to M1PAM with a high α value, Compound D has lower impact on ileum motility.

Example 26: Similar to Donepezil, Both Compound D and Compound C Improved Scopolamine-Induced Cognitive Deficits in Rats in NORT Next, the effects of M1PAMs, Compound D and Compound C, on recognition memory performance of rats in NORT were assessed using donepezil as a control. Scopolamine-induced cognitive deficit has been used as a model of cognitive impairment associated with cholinergic deficits in animals and human. Donepezil at 0.3 and 1 mg/kg significantly increased NDI in recognition memory trials (P≤0.025, FIG. 8A). Like donepezil, Compound D at 0.3, 1, and 3 mg/kg significantly increased NDI in scopolamine-induced deficits (0.3 mg/kg is minimal efficacy dose of Compound D in rats) (P≤0.025, FIG. 8B-C). Compound C at 0.1 and 0.3 mg/kg also significantly ameliorated scopolamine-induced cognitive deficits (0.1 mg/kg is minimal efficacy dose of Compound C in rats) (P≤0.025, FIG. 8D). Thus, Compound D, Compound C, and donepezil might selectively improve cognitive dysfunction associated with cholinergic deficits in rats.

Example 27: M1PAMs have Lower Risks of Cholinergic Side Effect than Donepezil

Donepezil, Compound D, and Compound C induced diarrhea dose-dependently in rats (P≤0.025 at 10 and 30 mg/kg, FIG. 9A; P≤0.025 at 10 and 30 mg/kg (10 mg/kg is minimal diarrhea inducing dose of Compound D in rats), FIG. 9B; P≤0.025 at 0.1 and 0.3 mg/kg (0.1 mg/kg is minimal diarrhea inducing dose of Compound C in rats), FIG. 9C). Cholinergic side effects of donepezil, Compound 0, and Compound C in rats were shown in Table 6. In addition to diarrhea, donepezil at 10 mg/kg, p.o. induced salivation, myosis, and fasciculation, whereas Compound D up to 30 mg/kg and Compound C up to 0.3 mg/kg did not induce other cholinergic side effects than diarrhea in rats.

Example 28: Combination of Sub-Effective Dose of Compound D and Donepezil Improve Scopolamine-Induced Cognitive Deficits in NORT in Rats Based on the pharmacological mechanisms of M1PAM and acetylcholinesterase inhibitors, synergistic effect between Compound D and donepezil can be expected. Combination of Compound D (3 mg/kg) with donepezil (3 mg/kg) induced more robust increase of IP1 production compared to monotherapy of each compound in rat hippocampus (FIG. 10A). Effects of the combination at sub-effective doses of Compound D (0.1 mg/kg) and donepezil (0.1 mg/kg) on scopolamine-induced deficits in NORT was evaluated. In the acquisition trial, these drug treatments did not affect the exploration time. Control rats discriminated a novel object from familiar one with 67.6% NDI in the retention trial after a 4 h ITI, whereas scopolamine-treated rats failed to discriminate a novel object from familiar one and showed significantly lower NDI (52.7%) (FIG. 10B). Compound D at 0.1 mg/kg and donepezil at 0.1 mg/kg alone did not affect NDI (54.1% and 52.7%, respectively, FIG. 10B), and the combination use of 0.1 mg/kg of Compound D and donepezil significantly increased NDI (63.0%) compared with vehicle-treated group in scopolamine-treated rats

TABLE 6

M1PAMs have lower risks of cholinergic side effect other than diarrhea than donepezil.

| Drug | Dose (mg/kg, p.o.) | Diarrhea | Lacrimation | Salivation | Myosis | Fasciculation |
|---|---|---|---|---|---|---|
| Vehicle | 0 | 0/6 (0%) | 0/6 (0%) | 0/6 (0%) | 0/6 (0%) | 0/6 (0%) |
| Donepezil | 1 | 0/6 (0%) | 0/6 (0%) | 0/6 (0%) | 0/6 (0%) | 0/6 (0%) |
| Donepezil | 3 | 0/6 (0%) | 0/6 (0%) | 0/6 (0%) | 0/6 (0%) | 0/6 (0%) |
| Donepezil | 10 | 3/6 (50%) | 0/6 (0%) | 1/6 (17%) | 5/6 (83%) | 6/6 (100%) |
| Donepezil | 30 | 3/6 (50%) | 0/6 (0%) | 4/6 (67%) | 6/6 (100%) | 6/6 (100%) |
| Compound D | 1 | 0/6 (0%) | 0/6 (0%) | 0/6 (0%) | 0/6 (0%) | 0/6 (0%) |
| Compound D | 3 | 1/6 (17%) | 0/6 (0%) | 0/6 (0%) | 0/6 (0%) | 0/6 (0%) |
| Compound D | 10 | 5/6 (83%) | 0/6 (0%) | 0/6 (0%) | 0/6 (0%) | 0/6 (0%) |
| Compound D | 30 | 4/6 (67%) | 0/6 (0%) | 0/6 (0%) | 0/6 (0%) | 0/6 (0%) |
| Compound C | 0.01 | 0/6 (0%) | 0/6 (0%) | 0/6 (0%) | 0/6 (0%) | 0/6 (0%) |
| Compound C | 0.03 | 0/6 (0%) | 0/6 (0%) | 0/6 (0%) | 0/6 (0%) | 0/6 (0%) |
| Compound C | 0.1 | 3/6 (50%) | 0/6 (0%) | 0/6 (0%) | 0/6 (0%) | 0/6 (0%) |
| Compound C | 0.3 | 4/6 (67%) | 0/6 (0%) | 0/6 (0%) | 0/6 (0%) | 0/6 (0%) |

After treatment with donepezil, Compound D, or Compound C, rats were observed for 240 min. For diarrhea, the number of rats scored more than or equal to 2 was counted. For fasciculation, the number of rats with marked fasciculation of both the upper and lower limbs was counted. For lacrimation, the number of rats in which moderate to marked discharge (severer lacrimation than fluid around eyes) was counted. For salivation, the number of rats with severe salivation, but not just noticeably wet around mouth, was counted. The maximum score during the observation was adopted. Data were presented as the number of incidence per total rats. Incidence ratio (%) was noted in parentheses.

Figure 11A:
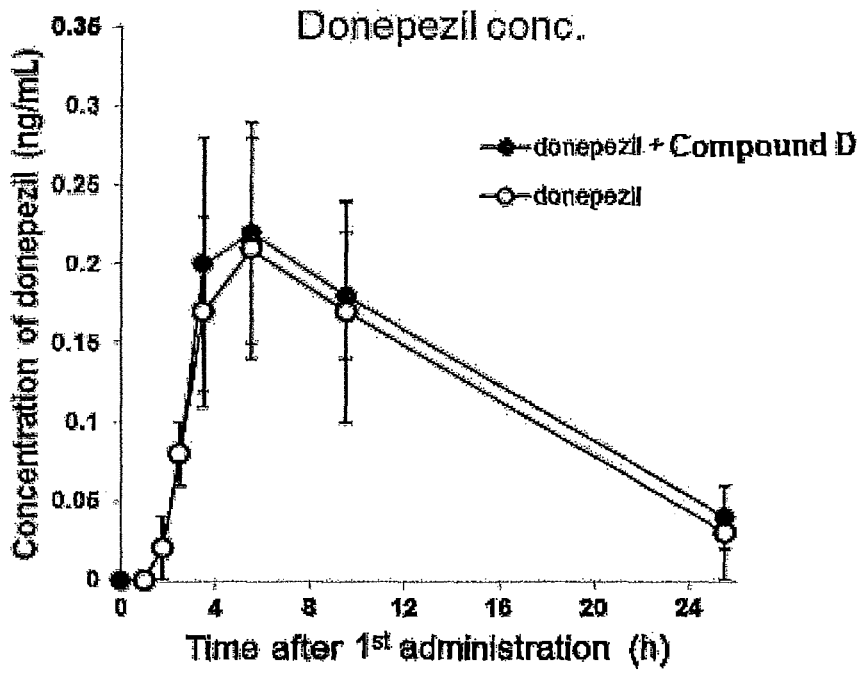
FIG. 11A-11B depicts Compound D does not affect the pharmacokinetics of donepezil (Example 28).
Figure 11B:
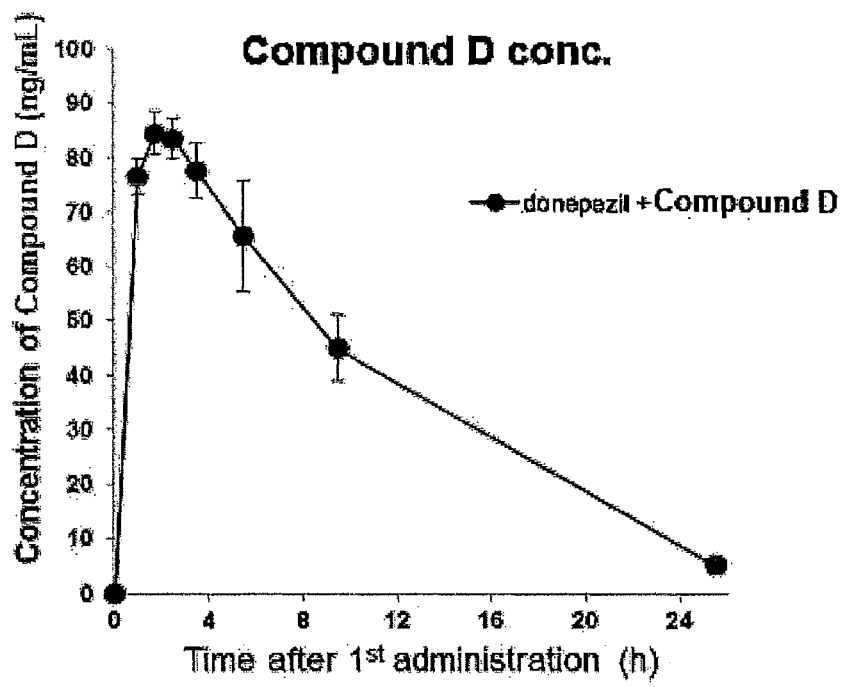

(P≤0.05, FIG. 10B). No significant differences in PK profile of donepezil were observed between compound alone and combination with Compound D (FIG. 11), thus, sub-effective dose of Compound D and donepezil would have a synergistic effect in cognitive improvement in scopolamine-treated rats.

Side effect profile after co-administration of Compound D and donepezil was also characterized in rats. Effective dosages of both Compound D and donepezil in cognitive improvement in rats was 0.3 mg/kg. Combination of Compound D (1 mg/kg) and donepezil (0.3 mg/kg) did not show any cholinergic-related side effects in rats (Table 7).

TABLE 7

Combination of Compound D and donepezil did not affect any cholinergic side effects in rats.

| Group (dose, mg/kg, p.o.) | Diarrhea | Lacrimation | Salivation | Myosis | Fasciculation |
|---|---|---|---|---|---|
| Vehicle | 0/6 (0%) | 0/6 (0%) | 0/6 (0%) | 0/6 (0%) | 0/6 (0%) |
| Donepezil (0.3) | 0/6 (0%) | 0/6 (0%) | 0/6 (0%) | 0/6 (0%) | 0/6 (0%) |
| Compound D (3) | 1/6 (17%) | 0/6 (0%) | 0/6 (0%) | 0/6 (0%) | 0/6 (0%) |
| Donepezil (0.3) + Compound D (1) | 0/6 (0%) | 0/6 (0%) | 0/6 (0%) | 0/6 (0%) | 0/6 (0%) |
| Donepezil (0.3) + Compound D (3) | 1/6 (17%) | 0/6 (0%) | 0/6 (0%) | 0/6 (0%) | 0/6 (0%) |

After treatment with donepezil alone, Compound D alone, and combination of both compounds, rats were observed for 240 min. For diarrhea, the number of rats scored more than or equal to 2 was counted. For fasciculation, the number of rats with marked fasciculation of both the upper and lower limbs was counted. For lacrimation, the number of rats in which moderate to marked discharge (severer lacrimation than fluid around eyes) was counted. For salivation, the number of rats with severe salivation, but not just noticeably wet around mouth, was counted. The maximum score during the observation was adopted. Data were presented as the number of incidence per total rats. Incidence ratio was noted in parentheses.

Example 29: Combination of Compound C and Donepezil at Sub-Effective Did not Improve Scopolamine-Induced Cognitive Deficits in NORT in Rats. (Comparative Example)

Effects of the combination Compound C (0.03 mg/kg) and donepezil (0.1 mg/kg) at sub-effective doses on scopolamine-induced deficits in NORT was evaluated. In acquisition trial, drug treatments did not affect the exploration time. Control rats discriminated a novel object from a familiar one with 65.6% NDI in the retention trial after a 4 hr ITI, whereas scopolamine-treated rats failed to discriminate a novel object from a familiar one, and showed significantly lower NDI of 51.1% (FIG. 12). Neither Compound C (0.03 mg/kg) alone nor donepezil (0.1 mg/kg) alone at sub-effective dose affect NDI (52.3% and 49.5%, respectively, FIG. 12). The combination of Compound C (0.03 mg/kg) and donepezil (0.1 mg/kg) did not significantly increase NDI (54.8%) compared with vehicle-treated group in scopolamine-treated rats (FIG. 12). Thus, combination of M1PAM with high α-value of more than 1000 and donepezil would not synergistically improve scopolamine-induced cognitive deficits in rats.

Example 30: Contrary to Carbachol and Compound C, Compound D Revealed Only ADP Generation M1Rs are known to contribute to the three cholinergic effects in layer 5 pyramidal neurons: the resting membrane potential (RMP) and physiological responses such as the after hyperpolarization (AHP) the after depolarization (ADP) that typically follow brief periods of action potential generation (Gulledge et al., J. Neurosci. 2009 Aug. 5; 29(31): 9888-9902). To investigate effects of M1 PAMs with different n value on brain function, cholinergic excitation by Compound D and Compound C were assessed. First, the muscarinic receptor agonist carbachol (10 M for 10 min) was tested by bath application (FIG. 13-A, FIG. 13-B, FIG. 13-C). Carbachol suppressed AHP following depolarizing current injections (FIG. 13C left), produced an ADP potential (FIG. 13C middle), and induced depolarization of the RMP (FIG. 13C right) in layer 5 pyramidal neurons. Under these conditions, Compound D at 10 μM produced significant ADP generation, but not depolarization of RMP and suppression of AHP (FIG. 13D). On the other hand, Compound C generated subthreshold changes in the RMP, suppressed the AHP, and generated an ADP (FIG. 13E).

Example 31: Combined Use of Compound D and Rivastigmine (Cognition, Side Effects)

Next, effects of the combination Compound D (0.1 mg/kg, p.o.) and rivastigmine (0.1 mg/kg, i.p.) at sub-effective dose on scopolamine-induced cognition deficits in NORT were examined. In the acquisition trial, drug treatments did not affect the exploration time. Control rats discriminated a novel object from a familiar one with NDI of 65.9% in the retention trial after a 4 hr ITI, whereas scopolamine-treated rats failed to discriminate a novel object from a familiar one, and showed significantly lower NDI of 53.7% (FIG. 14). Compound D at 0.1 mg/kg and rivastigmine at 0.1 mg/kg alone did not affect NDI (56.8% and 53.9%, respectively, FIG. 14). The combination use of 0.1 mg/kg of Compound D (p.o.) and rivastigmine (i.p.) significantly increased NDI (64.9%) compared with vehicle-treated group in scopolamine-treated rats (FIG. 14).

Side effect profiles after co-administration of Compound D and rivastigmine was also characterized in rats under the same treatment conditions as NORT. Combination of Compound D (0.1 mg/kg, p.o.) and rivastigmine (0.1 mg/kg, i.p.) did not show any cholinergic side effects in rats (Table 8).

TABLE 8

Combination of Compound D and rivastigmine did not affect any cholinergic side effects in rats.

| Group (dose, mg/kg) | Diarrhea | Convulsion | Lacrimation | Salivation | Myosis | Fasciculation |
|---|---|---|---|---|---|---|
| Vehicle | 0/6 (0%) | 0/6 (0%) | 0/6 (0%) | 0/6 (0%) | 0/6 (0%) | 0/6 (0%) |
| Rivastigmine (0.1, i.p.) | 0/6 (0%) | 0/6 (0%) | 0/6 (0%) | 0/6 (0%) | 1/6 (17%) | 0/6 (0%) |

TABLE 8-continued

Combination of Compound D and rivastigmine did not affect any cholinergic side effects in rats.

| Group (dose, mg/kg) | Diarrhea | Convulsion | Lacrimation | Salivation | Myosis | Fasciculation |
|---|---|---|---|---|---|---|
| Compound D (0.1, p.o.) | 0/6 (0%) | 0/6 (0%) | 0/6 (0%) | 0/6 (0%) | 1/6 (17%) | 0/6 (0%) |
| Rivastigmine (0.1, i.p.) + Compound D (0.1, p.o.) | 0/6 (0%) | 0/6 (0%) | 0/6 (0%) | 0/6 (0%) | 1/6 (17%) | 0/6 (0%) |

After treatment with rivastigmine alone, Compound D alone, or combination of both compounds, rats were observed for 240 min. For diarrhea, the number of rats in which loose or mucous stool, or diarrhea was induced was counted. For fasciculation, the number of rats with marked fasciculation of both the upper and lower limbs was counted. For lacrimation, the number of rats in which moderate to marked discharge (severe lacrimation than fluid around eyes) was caused was counted. For salivation, the number of rats with severe salivation, but not just noticeably wet around mouth was counted. The maximum score during the observation was adopted. Data were presented as the number of incidence per total rats. Incidence ration was noted in parentheses.

This application is based on a US provisional patent application No. 62/508,609 (filing date: May 19, 2017), the contents of which are incorporated in full herein.

INDUSTRIAL APPLICABILITY

The screening method of the present invention can efficiently select a cholinergic muscarinic M1 receptor positive allosteric modulator (M1PAM) with reduced cholinergic side effects, and is useful for finding M1PAM with reduced cholinergic side effects and effective for treating Alzheimer's disease and the like.

The invention claimed is:

1. A method for screening for a cholinergic muscarinic M1 receptor (M1R) positive allosteric modulator (M1PAM) with reduced cholinergic side effects, comprising the following steps (a) to (c):
   (a) contacting M1R or a partial peptide thereof with a test compound, acetylcholine (ACh) and detectable M1 antagonist,
   (b) measuring $\alpha$ value of the test compound, wherein the $\alpha$ value is calculated as $\alpha_{AB}$ from numeric formula (ii):

$$Y = \frac{\frac{[C]}{K_C} + \frac{\alpha_{BC}[B][C]}{K_B K_C}}{1 + \frac{[A]}{K_A} + \frac{[B]}{K_B} + \frac{[C]}{K_C} + \frac{\alpha_{AB}[A][B]}{K_A K_B} + \frac{\alpha_{AB}[B][C]}{K_B K_C}} ; \quad \text{(ii)}$$

wherein Y is the percentage of specific binding;
   [A], [B], and [C] are respectively the concentration of ACh, the test compound and detectable M1 antagonist;
   $K_A$, $K_B$ and $K_C$ respectively show the equilibrium dissociation constant of ACh, the test compound and detectable M1 antagonist; and
   $\alpha_{AB}$ and $\alpha_{BC}$ are respectively the cooperativities between the test compound and ACh, and the test compound and detectable M1 antagonist,
   (c) repeating steps (a) and (b) to screen one or more test compounds and selecting one or more of the test compounds with a low $\alpha$ value, each as an M1PAM, wherein the low a value is associated with reduced cholinergic side effects, and wherein the low $\alpha$ value is greater than 1 and not more than 500, and wherein the M1PAM with reduced cholinergic side effects has not less than 2-fold safety margin between a minimal cognition effective dose and a minimal cholinergic side effect dose in mammals.

2. The method for screening according to claim 1, wherein the low a value is greater than 10 and not more than 500.

3. The method for screening according to claim 1, wherein the cholinergic side effect is diarrhea.

4. A method for screening for a cholinergic muscarinic M1 receptor (M1R) positive allosteric modulator (M1PAM) with reduced cholinergic side effects, comprising the following steps (a) to (c):
(a) contacting M1R or a partial peptide thereof with a test compound and detectable ACh,
(b) measuring α value of the test compound, wherein the α value is calculated from numeric formula (i);

$$Y = \frac{\frac{[A]}{K_A} + \frac{\alpha[A][B]}{K_A K_B}}{1 + \frac{[A]}{K_A} + \frac{[B]}{K_B} + \frac{\alpha_{AB}[A][B]}{K_A K_B}}; \qquad (i)$$

where Y is the percentage of specific binding;
[A] and [B] are respectively the concentration of detectable ACh and the test compound;
$K_A$ and $K_B$ are respectively the equilibrium dissociation constant of detectable ACh and the test compound; and
α is the cooperativity between the test compound and detectable ACh,
(c) repeating steps (a) and (b) to screen one or more test compounds and selecting one or more of the test compounds with a low α value, each as an MIPAM, wherein the low α value is associated with reduced cholinergic side effects, and wherein the low α value is greater than 1 and not more than 500, and wherein the M1PAM with reduced cholinergic side effects has not less than 2-fold safety margin between a minimal cognition effective dose and a minimal cholinergic side effect dose in mammals.

5. The method for screening according to claim 4, wherein the low a value is greater than 10 and not more than 500.

6. The method for screening according to claim 4, wherein the cholinergic side effect is diarrhea.

7. A method for screening for a cholinergic muscarinic M1 receptor (M1R) positive allosteric modulator (M1PAM) with reduced cholinergic side effects, comprising the following steps (a) to (c):
(a) contacting M1R or a partial peptide thereof with a test compound, ACh, and detectable M1PAM,
(b) measuring α value of the test compound, wherein the α value can be calculated as $\alpha_{AB}$ from numeric formula (iii):

$$Y = \frac{\frac{[C]}{K_C} + \frac{\alpha_{AC}[A][C]}{K_A K_C}}{1 + \frac{[A]}{K_A} + \frac{[B]}{K_B} + \frac{[C]}{K_C} + \frac{\alpha_{AB}[A][B]}{K_A K_B} + \frac{\alpha_{AC}[A][C]}{K_A K_C}}; \qquad (iii)$$

wherein Y is the percentage of specific binding;
[A], [B], and [C] are respectively the concentration of ACh, the test compound and detectable M1PAM;
$K_A$, $K_B$ and $K_C$ respectively show the equilibrium dissociation constant of ACh, the test compound and detectable M1PAM; and
$\alpha_{AB}$ and $\alpha_{AC}$ are respectively the cooperativities between ACh and the test compound, and ACh and detectable M1PAM,
(c) repeating steps (a) and (b) to screen one or more test compounds and selecting one or more of the test compounds with a low α value, each as an MIPAM, wherein the low α value is associated with reduced cholinergic side effects, and wherein the low α value is greater than 1 and not more than 500, and wherein the M1PAM with reduced cholinergic side effects has not less than 2-fold safety margin between a minimal cognition effective dose and a minimal cholinergic side effect dose in mammals.

8. The method for screening according to claim 7, wherein the low a value is greater than 10 and not more than 500.

9. The method for screening according to claim 7, wherein the cholinergic side effect is diarrhea.

10. A method for treating a mammal, comprising administering a selected M1PAM of claim 1 and an acetylcholinesterase inhibitor to the mammal.

11. A method for treating a mammal, comprising administering a selected M1PAM of claim 4 and an acetylcholinesterase inhibitor to the mammal.

12. A method for treating a mammal, comprising administering a selected M1PAM of claim 7 and an acetylcholinesterase inhibitor to the mammal.

* * * * *

SEQUENCE LISTING

```
<160> NUMBER OF SEQ ID NOS: 5

<210> SEQ ID NO 1
<211> LENGTH: 1383
<212> TYPE: DNA
<213> ORGANISM: Homo sapiens
<220> FEATURE:
<221> NAME/KEY: CDS
<222> LOCATION: (1)..(1383)

<400> SEQUENCE: 1 atg aac act tca gcc cca cct gct gtc agc ccc aac atc acc gtc ctg      48
Met Asn Thr Ser Ala Pro Pro Ala Val Ser Pro Asn Ile Thr Val Leu
1               5                   10                  15 gca cca gga aag ggt ccc tgg caa gtg gcc ttc att ggg atc acc acg      96
Ala Pro Gly Lys Gly Pro Trp Gln Val Ala Phe Ile Gly Ile Thr Thr
            20                  25                  30 ggc ctc ctg tcg cta gcc aca gtg aca ggc aac ctg ctg gta ctc atc     144
Gly Leu Leu Ser Leu Ala Thr Val Thr Gly Asn Leu Leu Val Leu Ile
        35                  40                  45 tct ttc aag gtc aac acg gag ctc aag aca gtc aat aac tac ttc ctg     192
Ser Phe Lys Val Asn Thr Glu Leu Lys Thr Val Asn Asn Tyr Phe Leu
    50                  55                  60 ctg agc ctg gcc tgt gct gac ctc atc atc ggt acc ttc tcc atg aac     240
Leu Ser Leu Ala Cys Ala Asp Leu Ile Ile Gly Thr Phe Ser Met Asn
65                  70                  75                  80 ctc tat acc acg tac ctg ctc atg ggc cac tgg gct ctg ggc acg ctg     288
Leu Tyr Thr Thr Tyr Leu Leu Met Gly His Trp Ala Leu Gly Thr Leu
                85                  90                  95 gct tgt gac ctc tgg ctg gcc ctg gac tat gtg gcc agc aat gcc tcc     336
Ala Cys Asp Leu Trp Leu Ala Leu Asp Tyr Val Ala Ser Asn Ala Ser
            100                 105                 110 gtc atg aat ctg ctg ctc atc agc ttt gac cgc tac ttc tcc gtg act     384
Val Met Asn Leu Leu Leu Ile Ser Phe Asp Arg Tyr Phe Ser Val Thr
        115                 120                 125 cgg ccc ctg agc tac cgt gcc aag cgc aca ccc cgc cgg gca gct ctg     432
Arg Pro Leu Ser Tyr Arg Ala Lys Arg Thr Pro Arg Arg Ala Ala Leu
    130                 135                 140
```

```
atg atc ggc ctg gcc tgg ctg gtt tcc ttt gtg ctc tgg gcc cca gcc    480
Met Ile Gly Leu Ala Trp Leu Val Ser Phe Val Leu Trp Ala Pro Ala
145                 150                 155                 160 atc ctc ttc tgg cag tac ctg gta ggg gag cgg aca gtg cta gct ggg    528
Ile Leu Phe Trp Gln Tyr Leu Val Gly Glu Arg Thr Val Leu Ala Gly
                165                 170                 175 cag tgc tac atc cag ttc ctc tcc cag ccc atc atc acc ttt ggc aca    576
Gln Cys Tyr Ile Gln Phe Leu Ser Gln Pro Ile Ile Thr Phe Gly Thr
            180                 185                 190 gcc atg gct gcc ttc tac ctc cct gtc aca gtc atg tgc acg ctc tac    624
Ala Met Ala Ala Phe Tyr Leu Pro Val Thr Val Met Cys Thr Leu Tyr
        195                 200                 205 tgg cgc atc tac cgg gag aca gag aac cga gca cgg gag ctg gca gcc    672
Trp Arg Ile Tyr Arg Glu Thr Glu Asn Arg Ala Arg Glu Leu Ala Ala
    210                 215                 220 ctt cag ggc tcc gag acg cca ggc aaa ggg ggt ggc agc agc agc agc    720
Leu Gln Gly Ser Glu Thr Pro Gly Lys Gly Gly Gly Ser Ser Ser Ser
225                 230                 235                 240 tca gag agg tct cag cca ggg gct gag ggc tca cca gag act cct cca    768
Ser Glu Arg Ser Gln Pro Gly Ala Glu Gly Ser Pro Glu Thr Pro Pro
                245                 250                 255 ggc cgc tgc tgt cgc tgc tgc cgg gcc ccc agg ctg ctg cag gcc tac    816
Gly Arg Cys Cys Arg Cys Cys Arg Ala Pro Arg Leu Leu Gln Ala Tyr
            260                 265                 270 agc tgg aag gaa gaa gag gaa gag gac gaa ggc tcc atg gag tcc ctc    864
Ser Trp Lys Glu Glu Glu Glu Glu Asp Glu Gly Ser Met Glu Ser Leu
        275                 280                 285 aca tcc tca gag gga gag gag cct ggc tcc gaa gtg gtg atc aag atg    912
Thr Ser Ser Glu Gly Glu Glu Pro Gly Ser Glu Val Val Ile Lys Met
    290                 295                 300 cca atg gtg gac ccc gag gca cag gcc ccc acc aag cag ccc cca cgg    960
Pro Met Val Asp Pro Glu Ala Gln Ala Pro Thr Lys Gln Pro Pro Arg
305                 310                 315                 320 agc tcc cca aat aca gtc aag agg ccg act aag aaa ggg cgt gat cga    1008
Ser Ser Pro Asn Thr Val Lys Arg Pro Thr Lys Lys Gly Arg Asp Arg
                325                 330                 335 gct ggc aag ggc cag aag ccc cgt gga aag gag cag ctg gcc aag cgg    1056
Ala Gly Lys Gly Gln Lys Pro Arg Gly Lys Glu Gln Leu Ala Lys Arg
            340                 345                 350 aag acc ttc tcg ctg gtc aag gag aag aag gcg gct cgg acc ctg agt    1104
Lys Thr Phe Ser Leu Val Lys Glu Lys Lys Ala Ala Arg Thr Leu Ser
        355                 360                 365 gcc atc ctc ctg gcc ttc atc ctc acc tgg aca ccg tac aac atc atg    1152
Ala Ile Leu Leu Ala Phe Ile Leu Thr Trp Thr Pro Tyr Asn Ile Met
    370                 375                 380 gtg ctg gtg tcc acc ttc tgc aag gac tgt gtt ccc gag acc ctg tgg    1200
Val Leu Val Ser Thr Phe Cys Lys Asp Cys Val Pro Glu Thr Leu Trp
385                 390                 395                 400 gag ctg ggc tac tgg ctg tgc tac gtc aac agc acc atc aac ccc atg    1248
Glu Leu Gly Tyr Trp Leu Cys Tyr Val Asn Ser Thr Ile Asn Pro Met
                405                 410                 415 tgc tac gca ctc tgc aac aaa gcc ttc cgg gac acc ttt cgc ctg ctg    1296
Cys Tyr Ala Leu Cys Asn Lys Ala Phe Arg Asp Thr Phe Arg Leu Leu
            420                 425                 430 ctg ctt tgc cgc tgg gac aag aga cgc tgg cgc aag atc ccc aag cgc    1344
Leu Leu Cys Arg Trp Asp Lys Arg Arg Trp Arg Lys Ile Pro Lys Arg
        435                 440                 445 cct ggc tcc gtg cac cgc act ccc tcc cgc caa tgc tga    1383
Pro Gly Ser Val His Arg Thr Pro Ser Arg Gln Cys
```

```
                  450             455             460

<210> SEQ ID NO 2
<211> LENGTH: 460
<212> TYPE: PRT
<213> ORGANISM: Homo sapiens

<400> SEQUENCE: 2

Met Asn Thr Ser Ala Pro Pro Ala Val Ser Pro Asn Ile Thr Val Leu
1               5                   10                  15

Ala Pro Gly Lys Gly Pro Trp Gln Val Ala Phe Ile Gly Ile Thr Thr
            20                  25                  30

Gly Leu Leu Ser Leu Ala Thr Val Thr Gly Asn Leu Leu Val Leu Ile
        35                  40                  45

Ser Phe Lys Val Asn Thr Glu Leu Lys Thr Val Asn Asn Tyr Phe Leu
    50                  55                  60

Leu Ser Leu Ala Cys Ala Asp Leu Ile Ile Gly Thr Phe Ser Met Asn
65                  70                  75                  80

Leu Tyr Thr Thr Tyr Leu Leu Met Gly His Trp Ala Leu Gly Thr Leu
                85                  90                  95

Ala Cys Asp Leu Trp Leu Ala Leu Asp Tyr Val Ala Ser Asn Ala Ser
            100                 105                 110

Val Met Asn Leu Leu Leu Ile Ser Phe Asp Arg Tyr Phe Ser Val Thr
        115                 120                 125

Arg Pro Leu Ser Tyr Arg Ala Lys Arg Thr Pro Arg Arg Ala Ala Leu
    130                 135                 140

Met Ile Gly Leu Ala Trp Leu Val Ser Phe Val Leu Trp Ala Pro Ala
145                 150                 155                 160

Ile Leu Phe Trp Gln Tyr Leu Val Gly Glu Arg Thr Val Leu Ala Gly
                165                 170                 175

Gln Cys Tyr Ile Gln Phe Leu Ser Gln Pro Ile Ile Thr Phe Gly Thr
            180                 185                 190

Ala Met Ala Ala Phe Tyr Leu Pro Val Thr Val Met Cys Thr Leu Tyr
        195                 200                 205

Trp Arg Ile Tyr Arg Glu Thr Glu Asn Arg Ala Arg Glu Leu Ala Ala
    210                 215                 220

Leu Gln Gly Ser Glu Thr Pro Gly Lys Gly Gly Gly Ser Ser Ser Ser
225                 230                 235                 240

Ser Glu Arg Ser Gln Pro Gly Ala Glu Gly Ser Pro Glu Thr Pro Pro
                245                 250                 255

Gly Arg Cys Cys Arg Cys Cys Arg Ala Pro Arg Leu Leu Gln Ala Tyr
            260                 265                 270

Ser Trp Lys Glu Glu Glu Glu Asp Glu Gly Ser Met Glu Ser Leu
        275                 280                 285

Thr Ser Ser Glu Gly Glu Glu Pro Gly Ser Glu Val Val Ile Lys Met
    290                 295                 300

Pro Met Val Asp Pro Glu Ala Gln Ala Pro Thr Lys Gln Pro Pro Arg
305                 310                 315                 320

Ser Ser Pro Asn Thr Val Lys Arg Pro Thr Lys Lys Gly Arg Asp Arg
                325                 330                 335

Ala Gly Lys Gly Gln Lys Pro Arg Gly Lys Glu Gln Leu Ala Lys Arg
            340                 345                 350

Lys Thr Phe Ser Leu Val Lys Glu Lys Lys Ala Ala Arg Thr Leu Ser
        355                 360                 365
```

```
Ala Ile Leu Leu Ala Phe Ile Leu Thr Trp Thr Pro Tyr Asn Ile Met
    370             375                 380
Val Leu Val Ser Thr Phe Cys Lys Asp Cys Val Pro Glu Thr Leu Trp
385             390                 395                 400
Glu Leu Gly Tyr Trp Leu Cys Tyr Val Asn Ser Thr Ile Asn Pro Met
                405                 410                 415
Cys Tyr Ala Leu Cys Asn Lys Ala Phe Arg Asp Thr Phe Arg Leu Leu
                420             425                 430
Leu Leu Cys Arg Trp Asp Lys Arg Arg Trp Arg Lys Ile Pro Lys Arg
            435             440                 445
Pro Gly Ser Val His Arg Thr Pro Ser Arg Gln Cys
    450             455                 460

<210> SEQ ID NO 3
<211> LENGTH: 20
<212> TYPE: DNA
<213> ORGANISM: Artificial Sequence
<220> FEATURE:
<223> OTHER INFORMATION: forward primer

<400> SEQUENCE: 3
agctgaagcc acaaatgcag                                              20

<210> SEQ ID NO 4
<211> LENGTH: 19
<212> TYPE: DNA
<213> ORGANISM: Artificial Sequence
<220> FEATURE:
<223> OTHER INFORMATION: reverse primer

<400> SEQUENCE: 4
ctgagtcacg gagctgagc                                               19

<210> SEQ ID NO 5
<211> LENGTH: 26
<212> TYPE: DNA
<213> ORGANISM: Artificial Sequence
<220> FEATURE:
<223> OTHER INFORMATION: probe

<400> SEQUENCE: 5
agacctgaca tcctggcacc tcctgg                                       26
```